United States Patent
Hoque et al.

(10) Patent No.: US 9,978,689 B2
(45) Date of Patent: May 22, 2018

(54) ION SENSITIVE FIELD EFFECT TRANSISTORS WITH PROTECTION DIODES AND METHODS OF THEIR FABRICATION

(71) Applicants: Md M. Hoque, Gilbert, AZ (US);
Patrice Parris, Phoenix, AZ (US);
Weize Chen, Phoenix, AZ (US);
Richard De Souza, Chandler, AZ (US)

(72) Inventors: Md M. Hoque, Gilbert, AZ (US);
Patrice Parris, Phoenix, AZ (US);
Weize Chen, Phoenix, AZ (US);
Richard De Souza, Chandler, AZ (US)

(73) Assignee: NXP USA, INC., Austin, TX (US)

( * ) Notice: Subject to any disclaimer, the term of this patent is extended or adjusted under 35 U.S.C. 154(b) by 0 days. days.

(21) Appl. No.: 14/133,217

(22) Filed: Dec. 18, 2013

(65) Prior Publication Data
US 2015/0171018 A1 Jun. 18, 2015

(51) Int. Cl.
*H01L 23/552* (2006.01)
*G01N 27/403* (2006.01)
*G01N 27/414* (2006.01)
*H01L 23/60* (2006.01)
*H01L 29/66* (2006.01)

(52) U.S. Cl.
CPC .......... *H01L 23/552* (2013.01); *G01N 27/414* (2013.01); *H01L 23/60* (2013.01); *H01L 29/66825* (2013.01); *H01L 2924/0002* (2013.01)

(58) Field of Classification Search
CPC .............................. H01L 23/552; H01L 23/60
USPC ......................................................... 257/253
See application file for complete search history.

(56) References Cited

U.S. PATENT DOCUMENTS

| 4,589,970 | A | 5/1986 | Ligtenberg et al. |
| 5,414,284 | A | 5/1995 | Baxter et al. |
| 5,946,574 | A * | 8/1999 | Hsiao .................. H01L 21/8234 257/328 |
| 7,932,562 | B2 * | 4/2011 | Ono ..................... H01L 27/0255 257/362 |
| 8,263,336 | B2 | 9/2012 | Rothberg et al. |
| 2006/0175663 | A1 * | 8/2006 | Jeon .................... H01L 27/0262 257/355 |

(Continued)

OTHER PUBLICATIONS

Al-Ahdal, et al., "ISFET threshold voltage programming in CMOS using electron tunneling", Electronics Letters vol. 47, No. 25, pp. 1-2, Dec. 8, 2011.

*Primary Examiner* — Sitaramarao S Yechuri
(74) *Attorney, Agent, or Firm* — Sherry W. Schumm

(57) ABSTRACT

An embodiment of an Ion Sensitive Field Effect Transistor (ISFET) structure includes a substrate, source and drain regions formed within the substrate and spatially separated by a channel region, a gate dielectric and a gate formed over the channel region, multiple conductive structures overlying the surface of the substrate, and one or more protection diode circuits coupled between one or more of the multiple conductive structures and the substrate. The multiple conductive structures include a floating gate structure and a sense plate structure. The floating gate structure is formed over the gate dielectric and includes the gate. The sense plate structure is electrically coupled to the floating gate structure and is configured to sense a concentration of a target ion or molecule in a fluid adjacent to a portion of the sense plate structure.

16 Claims, 11 Drawing Sheets

(56) References Cited

U.S. PATENT DOCUMENTS

| | | | |
|---|---|---|---|
| 2009/0079414 A1 | 3/2009 | Levon et al. | |
| 2010/0301398 A1* | 12/2010 | Rothberg | G01N 27/4145 257/253 |
| 2010/0321843 A1* | 12/2010 | Domanski | H01L 27/0262 361/56 |
| 2011/0299337 A1* | 12/2011 | Parris | G05F 1/575 365/185.18 |
| 2013/0134479 A1* | 5/2013 | Xu | H01L 27/0262 257/173 |
| 2014/0197450 A1* | 7/2014 | He | H01L 27/0248 257/133 |
| 2014/0234981 A1* | 8/2014 | Zarkesh-Ha | C12Q 1/6869 436/94 |

* cited by examiner

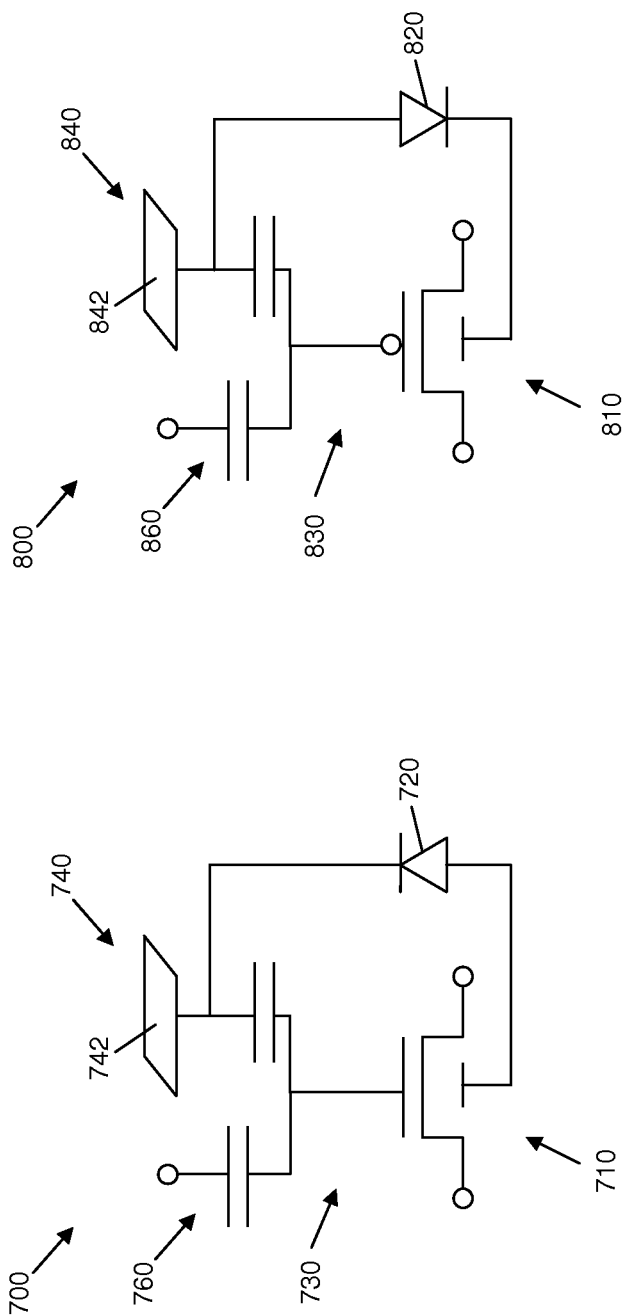

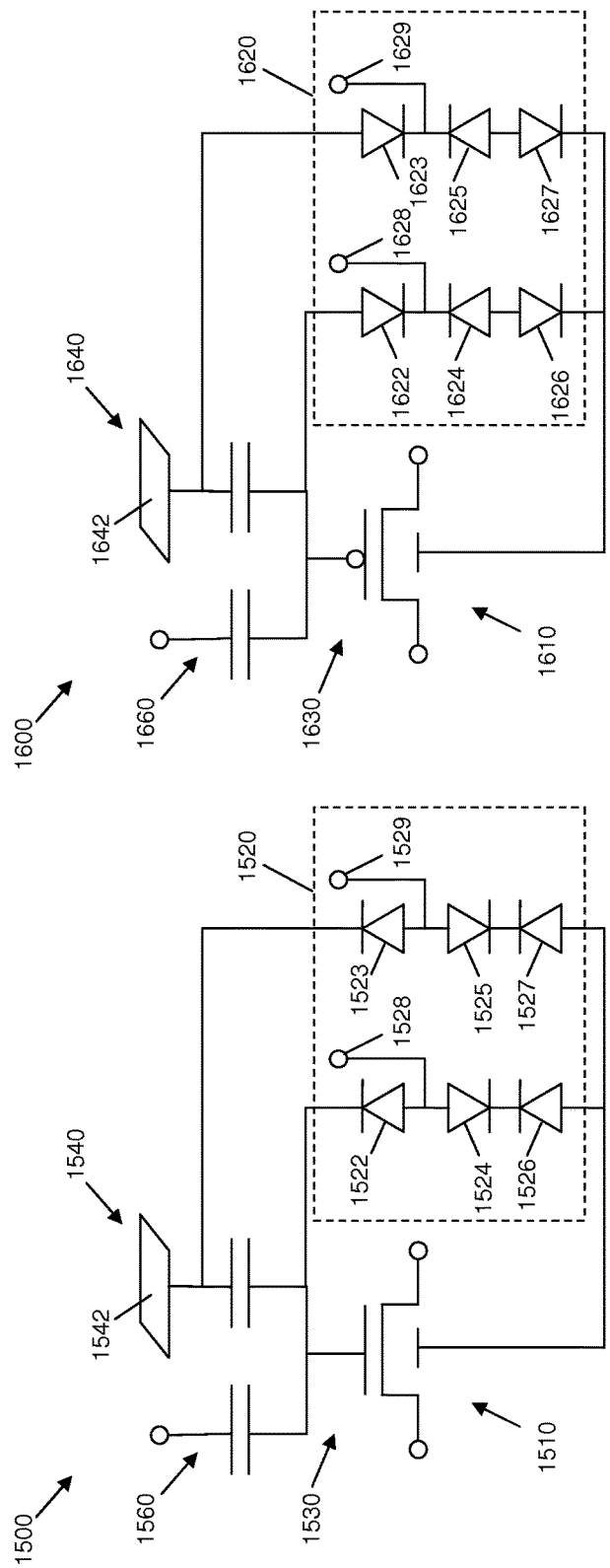

ION SENSITIVE FIELD EFFECT TRANSISTORS WITH PROTECTION DIODES AND METHODS OF THEIR FABRICATION

TECHNICAL FIELD

Embodiments of the subject matter described herein relate generally to semiconductor devices, and more particularly relate to Ion Sensitive Field Effect Transistors (ISFETs) and methods of their fabrication.

BACKGROUND

Ion Sensitive Field Effect Transistors (ISFETs) are often used to sense the concentration of a target ion or molecule in an electrolytic solution. In early ISFET designs, the fluid being sensed was often in intimate contact with the gate dielectric, or separated from the gate dielectric by an ion-sensitive membrane. Ultimately, however, CMOS process flows were used to create relatively low-cost ISFET structures with improved manufacturability.

A typical CMOS ISFET includes a sense plate and a CMOS transistor, which includes a floating gate that is coupled to the sense plate. As is typical with a CMOS transistor, the gate is electrically isolated from the transistor channel through a gate dielectric. During fabrication of a typical CMOS ISFET, once the gate dielectric is formed, it is susceptible to damage, particularly plasma-induced damage from fabrication processes in which plasma phenomena are present. These processes include, for example, plasma etching processes, plasma deposition processes, and so on. Even after fabrication, the gate dielectric may be susceptible to damage from electrostatic discharge (ESD) events or other situations in which the breakdown voltage of the gate dielectric is exceeded.

Accordingly, there is a need for improved ISFET devices that are less susceptible to plasma-induced and/or ESD-induced gate dielectric damage and which are manufacturable using conventional CMOS semiconductor processes.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 7 is a simplified circuit representation of an n-channel ISFET with a protection diode, according to yet another example embodiment;

FIG. 8 is a simplified circuit representation of a p-channel ISFET with a protection diode, according to yet another example embodiment;

FIG. 15 is a simplified circuit representation of an n-channel ISFET with first and second biased series of protection diodes, according to yet another example embodiment;

FIG. 16 is a simplified circuit representation of a p-channel ISFET with first and second biased series of protection diodes, according to yet another example embodiment.

DETAILED DESCRIPTION

Figure 2:
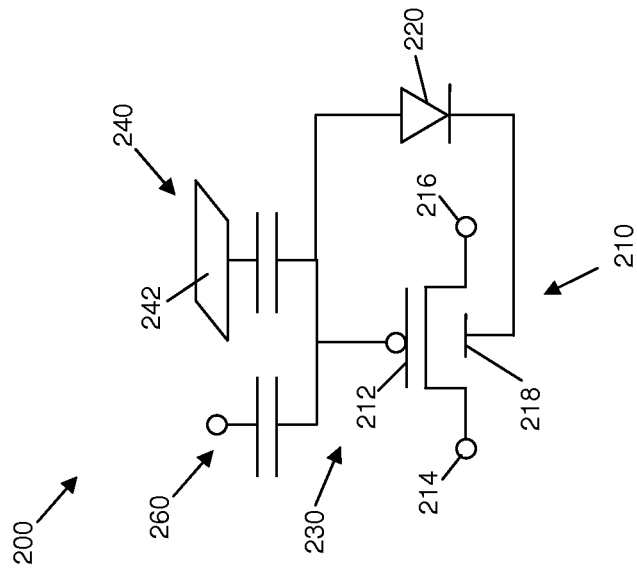
FIG. 2 is a simplified circuit representation of a p-channel ISFET with a protection diode, according to an example embodiment.

The following detailed description is merely exemplary in nature and is not intended to limit the embodiments or the application and uses of the various embodiments. Furthermore, there is no intention to be bound by any expressed or implied theory presented in the preceding technical field or background, or the following detailed description.

For simplicity and clarity of illustration, the drawing figures illustrate the general manner of construction, and descriptions and details of well-known features and techniques may be omitted to avoid unnecessarily obscuring the description of the embodiments. Additionally, elements in the drawings figures are not necessarily drawn to scale. For example, the dimensions of some of the elements or regions in some of the figures may be exaggerated relative to other elements or regions of the same or other figures to help improve understanding of the various embodiments.

The terms "first," "second," "third," "fourth" and the like in the description and the claims, if any, may be used for distinguishing between similar elements and not necessarily for describing a particular sequential or chronological order. It is to be understood that the terms so used are interchangeable under appropriate circumstances such that the embodiments described herein are, for example, capable of use in sequences other than those illustrated or otherwise described herein. Furthermore, the terms "comprise," "include," "have" and any variations thereof, are intended to cover non-exclusive inclusions, such that a process, method, article, or apparatus that comprises a list of elements is not necessarily limited to those elements, but may include other elements not expressly listed or inherent to such process, method, article, or apparatus. The terms "left," right," "in,"

"out," "front," "back," "up," "down, "top," "bottom," "over," "under," "above," "below" and the like in the description and the claims, if any, are used for describing relative positions and not necessarily for describing permanent positions in space. It is to be understood that the embodiments described herein may be used, for example, in other orientations than those illustrated or otherwise described herein. The term "coupled," as used herein, is defined as directly or indirectly connected in an electrical or non-electrical manner.

The various embodiments of the invention described here are illustrated by semiconductor devices and structures of particular conductivity type having various p and n doped regions appropriate for that conductivity type device or structure. But this is merely for convenience of explanation and not intended to be limiting. Persons of skill in the art will understand that devices or structures of opposite conductivity type may be provided by interchanging conductivity types so that a p-type region becomes an n-type region and vice versa. Alternatively, the particular regions illustrated in what follows may be more generally referred to as of a "first conductivity type" and a "second opposite conductivity type," wherein the first conductivity type may be either n or p type and the second opposite conductivity type is then either p or n type, and so forth. Further, for convenience of explanation and not intended to be limiting, various embodiments of the present invention are described herein for silicon semiconductors, but persons of skill in the art will understand the invention is not limited to silicon but applies to a wide variety of semiconductor materials. Non-limiting examples are other type IV semiconductor materials, as well as type III-V and II-VI semiconductor materials, organic semiconductor materials and combinations thereof, whether in bulk form or in layered form or in thin film form or semiconductor-on-insulator (SOI) form or combinations thereof. Such materials may be single-crystal or poly-crystalline or amorphous or combinations thereof.

Various embodiments of Ion Sensitive Field Effect Transistor (ISFET) structures (referred to simply as "ISFETs") and methods of their fabrication are discussed herein. The ISFET structures each include an insulated gate field effect transistor (IGFET) that includes a floating gate structure, and a sense plate structure electrically coupled (e.g., capacitively coupled) to the floating gate structure. In various embodiments, the ISFET may include an n-channel IGFET (e.g., the ISFET may be an n-channel ISFET) or a p-channel IGFET (e.g., the ISFET may be a p-channel ISFET), in various embodiments. The sense plate structure includes a conductive plate that is configured to sense the concentration of a target ion or molecule in a fluid adjacent to a portion of the sense plate structure. In addition, according to various embodiments, the ISFET structures each include one or more protection diode circuits coupled to either or both the floating gate structure and the sense plate structure. The protection diode circuit(s) are configured to decrease the likelihood of gate dielectric damage due to plasma phenomena during device fabrication and/or due to electrostatic discharge (ESD) events that occur during fabrication, device handling, or device operation.

Figure 1:
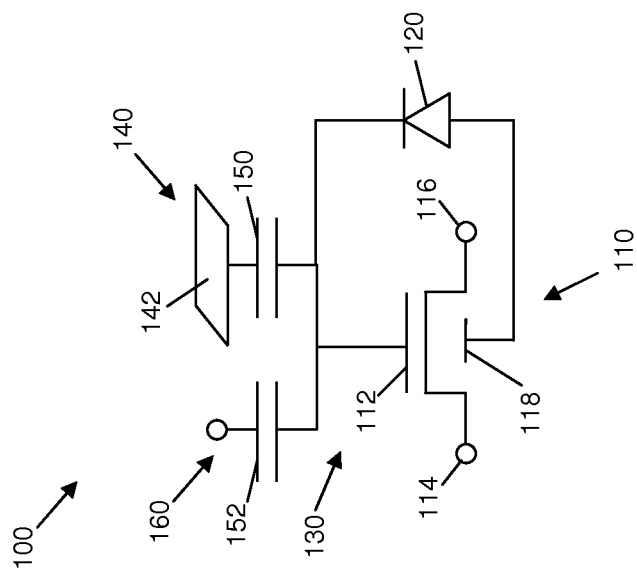
FIG. 1 is a simplified circuit representation of an n-channel ISFET with a protection diode, according to an example embodiment.

FIG. 1 is a simplified circuit representation of an n-channel ISFET 100 with a protection diode 120, according to an example embodiment. More specifically, ISFET 100 includes an n-channel IGFET 110, a floating gate structure 130, a sense plate structure 140, and a protection diode 120. IGFET 110 includes a gate 112, a source region, a drain region, and a body region 118. The source and drain regions are electrically coupled to source and drain contacts 114, 116, respectively.

Gate 112 forms a portion of floating gate structure 130, which also includes one or more conductive structures that are capacitively coupled (as indicated by capacitor 150) with sense plate structure 140. Sense plate structure 140 includes a sense plate 142 (e.g., a metal plate) configured to sense the concentration of a target ion or molecule in a fluid (not illustrated) adjacent to the sense plate 142, and additional conductive structures that facilitate the capacitive coupling between the sense plate structure 140 and the floating gate structure 130. In general, during operation of ISFET 100, the concentration of a target ion or molecule within the fluid results in a corresponding electrical bias of the floating gate structure 130. More specifically, the gate bias affects the conductivity of the channel, which may result in a current signal between the source and drain contacts 114, 116 that is dependent upon the target ion or molecule concentration within the fluid. Detection circuitry (not illustrated) coupled to the source and/or drain contacts 114, 116 may determine the target ion or molecule concentration within the fluid based on the current signal.

Protection diode 120 includes a cathode coupled to the floating gate structure 130 and an anode coupled to the body region 118 of IGFET 110, as illustrated in FIG. 1. In an alternate embodiment, protection diode 120 may have an anode coupled to another region having the same conductivity type as the body region 118. According to an embodiment, protection diode 120 may be a PN junction diode (e.g., a zener diode) with a reverse breakdown voltage that is higher than a typical operating voltage that may be applied to the gate 112, but lower than the breakdown voltage of a gate dielectric between gate 112 and the channel region of IGFET 110. In an alternate embodiment, protection diode 120 may be another type of diode (e.g., a Schottky diode, a discrete diode, or some other type of diode). During fabrication of the ISFET 100, plasma induced charges on the floating gate structure 130 may be discharged through the protection diode 120 into the substrate. This may protect the gate dielectric of the IGFET 110 from plasma-induced damage, and thus may improve device yields and/or reliability.

According to an embodiment, ISFET 100 also may include a control gate structure 160, which is capacitively coupled (as indicated by capacitor 152) to the floating gate structure 130. The control gate structure 160 may be used during programming of ISFET 100, for example, and/or may be used to receive a bias voltage and effect movement of charge between the floating gate structure 130 and the control gate structure 160. More specifically, the control gate structure 160 may be utilized to trim the threshold voltage of the ISFET 100 to a desired value.

FIG. 2 is a simplified circuit representation of a p-channel ISFET 200 with a protection diode 220 (e.g., a zener diode, PN junction diode, or other type of diode), according to an example embodiment. In contrast with ISFET 100 (FIG. 1), ISFET 200 includes a p-channel IGFET 210, and a protection diode 220 with an anode coupled to a floating gate structure 230 of the ISFET 200 and a cathode coupled to a body region 218 of IGFET 210, as illustrated in FIG. 2. In an alternate embodiment, protection diode 220 may have a cathode coupled to another region having the same conductivity type as the body region 218.

Similar to ISFET 100, IGFET 210 also includes a gate 212 that forms a portion of the floating gate structure 230, a source region coupled to a source contact 214, and a drain region coupled to a drain contact 216. In addition, ISFET 200 includes a sense plate structure 240 with a sense plate 242, where the sense plate structure 240 is capacitively coupled with the floating gate structure 230. ISFET 200 also may include a control gate structure 260, which is capacitively coupled to the floating gate structure 230.

Figure 3:
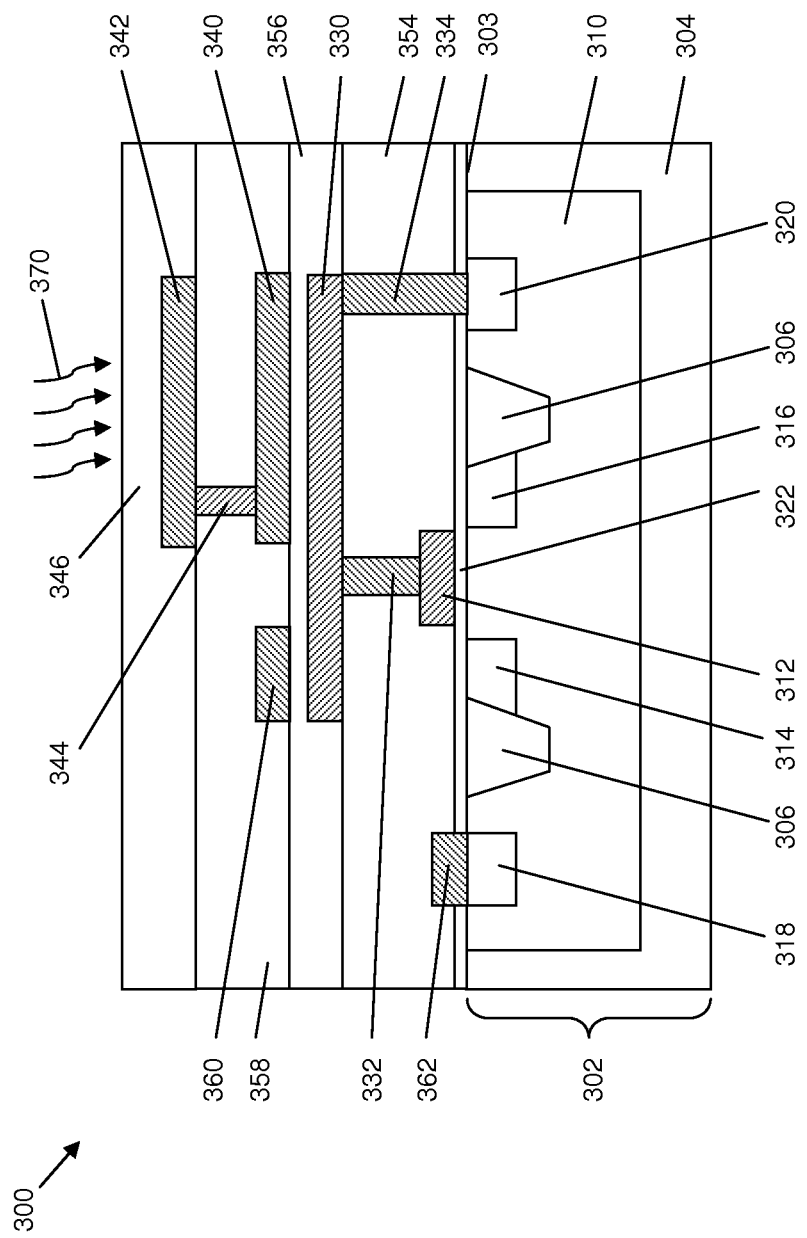
FIG. 3 is a cross-sectional view of an n-channel or p-channel ISFET with a protection diode, according to an example embodiment.

The circuit representations depicted in FIGS. 1 and 2 may be physically realized using a semiconductor structure, such as the structure depicted in FIG. 3. More specifically, FIG. 3 is a cross-sectional view of an ISFET 300 with a protection diode coupled to a floating gate structure, according to an example embodiment. ISFET 300 may be an n-channel device or a p-channel device, depending on the selected conductivities of various regions of ISFET 300. To generalize the description of ISFET 300, various regions of ISFET 300 will be described below as having a "first conductivity type" or a "second conductivity type." In an embodiment in which the "first conductivity type" is p-type and the "second conductivity type" is n-type, ISFET 300 corresponds to an n-channel device (e.g., as in the ISFET embodiment represented by the circuit of FIG. 1). Conversely, in an embodiment in which the "first conductivity type" is n-type and the "second conductivity type" is p-type, ISFET 300 corresponds to a p-channel device (e.g., as in the ISFET embodiment represented by the circuit of FIG. 2).

ISFET 300 is formed in and on a semiconductor substrate 302, which has a top substrate surface 303. The semiconductor substrate 302 includes a base substrate 304 of either the first or second conductivity type, and a well region 310 (or body region) of the first conductivity type. Further, ISFET 300 includes an IGFET formed in and over an active region of the substrate 302. According to an embodiment, the IGFET includes source and drain regions 314, 316 of the second conductivity type formed within well region 310, and spatially separated from each other across the top surface 303 of the substrate 302. The portion of the substrate 302 between the source and drain regions 314, 316 defines a channel region, and the IGFET further includes a gate dielectric 322 and a gate 312 formed over the channel region. The gate 312 may be a polysilicon gate, according to an embodiment. In an alternate embodiment, the gate 312 may be formed from a metal or metal alloy.

The gate 312 forms a portion of a floating gate structure (e.g., floating gate structure 130, 230, FIGS. 1, 2) that is formed in, on, and through one or more dielectric layers 354 overlying the top surface 303 of the substrate 302. The floating gate structure also includes at least one conductor 330 formed in at least one metal layer, and at least one conductive via 332 electrically coupling the conductor(s) 330 to the gate 312.

A sense plate structure (e.g., sense plate structure 140, 240, FIGS. 1, 2) is formed in, on, and through one or more dielectric layers 358 overlying the floating gate structure. According to an embodiment, the sense plate structure includes a metal sense plate 342 that is configured to sense the concentration of a target ion or molecule in a fluid 370 adjacent to a portion of the sense plate 342. According to an embodiment, the sense plate 342 is formed in a top metal layer of the ISFET 300. In order to protect the sense plate 342 from corrosion, oxidation and/or other damage, a passivation layer 346 may be formed over the sense plate 342. In other embodiments, the passivation layer 346 may be excluded (e.g., the sense plate 342 is directly exposed to the environment), or other types of layers may be formed over the sense plate 342 (e.g., a gold layer, another bio-compatible metal layer, a film specific to the target ion or molecule to be detected, and so on). The sense plate structure also includes at least one conductor 340 formed in at least one metal layer below the layer within which the sense plate 342 is formed, along with at least one conductive via 344 electrically coupling the conductor(s) 340 to the sense plate 342.

According to an embodiment, the floating gate structure and the sense plate structure are capacitively coupled. More specifically, a top conductor 330 of the floating gate structure is aligned with a bottom conductor 340 of the sense plate structure, and the conductors 330, 340 are electrically isolated from each other through dielectric layer 356. The conductors 330, 340 function as capacitor electrodes, and the dielectric layer 356 functions as the capacitor dielectric.

ISFET 300 also includes a protection diode (e.g., protection diode 120, 220, FIGS. 1, 2) electrically coupled to the floating gate structure through one or more conductive vias 334 and possibly other conductive features, in an embodiment. For example, the protection diode may be implemented as a PN junction diode (or zener diode) that is electrically coupled between the floating gate structure and the well region 310. According to an embodiment, ISFET 300 includes a diode region 320 of the second conductivity type formed within well region 310, and the PN junction established between diode region 320 and the well region 310 functions as the protection diode. In an embodiment in which the well region 310 has p-type conductivity and the diode region 320 has n-type conductivity (e.g., as in the ISFET embodiment represented by the circuit of FIG. 1), the diode region 320 functions as a cathode of the protection diode. Conversely, in an embodiment in which the well region 310 has n-type conductivity and the diode region 320 has p-type conductivity (e.g., as in the ISFET embodiment represented by the circuit of FIG. 2), the diode region 320 functions as an anode of the protection diode. In an alternate embodiment, a PN junction that functions as a protection diode may include a PN junction between the source and/or drain region 314, 316 and the well region 310. In other words, the source and/or drain regions 314, 316 may function as the cathode or anode of the protection diode, and diode region 320 may be excluded.

As indicated previously, the breakdown voltage of the protection diode (i.e., the breakdown voltage of the PN junction established between diode region 320 and well region 310) is higher than a typical operating voltage that may be applied to the gate 312, but lower than the breakdown voltage of gate dielectric 322. During fabrication of the ISFET 300, once the floating gate structure has been formed and coupled with the protection diode, plasma induced charges on the floating gate structure generated during further fabrication processes may be discharged through the protection diode into the substrate (or more particularly through diode region 320 into well region 310), thus protecting the gate dielectric 322 from plasma-induced damage.

In further embodiments, ISFET 300 may include additional features. For example, ISFET 300 also may include body contact region 318 of the first conductivity type and more heavily doped than the well region 310, in an embodiment. In addition, ISFET 300 may also include various shallow trench isolation (STI) structures 306 adjacent to the source and drain regions 314, 316, in an embodiment. In an alternate embodiment, the STI structures 306 may be replaced with a silicide blocking layer that prevents silicide formation at the surface 303 that may otherwise short various regions together.

Further, ISFET 300 also may include a control gate structure 360, which is capacitively coupled to the floating gate structure (e.g., to conductor 330 of the floating gate structure). ISFET 300 also may include additional contacts (e.g., a source contact (not illustrated), drain contact (not illustrated), and body contact 362) and other conductive structures that provide for electrical connection of various portions of ISFET 300 to other circuitry (not illustrated). Further, although the floating gate structure has been depicted to include only one metal layer (e.g., including conductor 330) and one via (i.e., via 332) extending through a single dielectric layer (i.e., dielectric layer 354), the floating gate structure may include more conductive features formed in, on, and through more dielectric layers. Similarly, although the sense plate structure has been depicted to include only two metal layers (e.g., including sense plate 342 and conductor 340) and one via (i.e., via 344) extending through a single dielectric layer (i.e., dielectric layer 358), the sense plate structure also may include more conductive features formed in, on, and through more dielectric layers. The same may be said for the other ISFET embodiments depicted in the other figures and described below.

Figure 5:
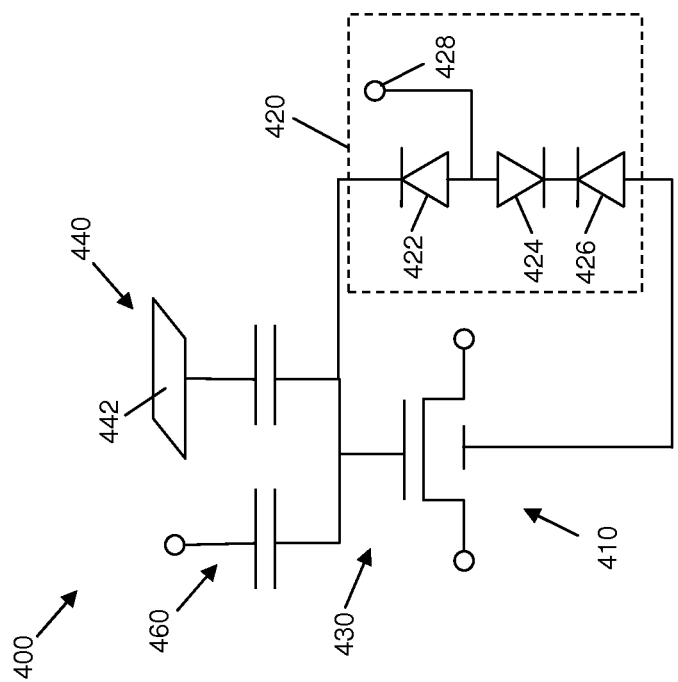
FIG. 5 is a simplified circuit representation of a p-channel ISFET with a biased series of protection diodes, according to another example embodiment.
Figure 6:
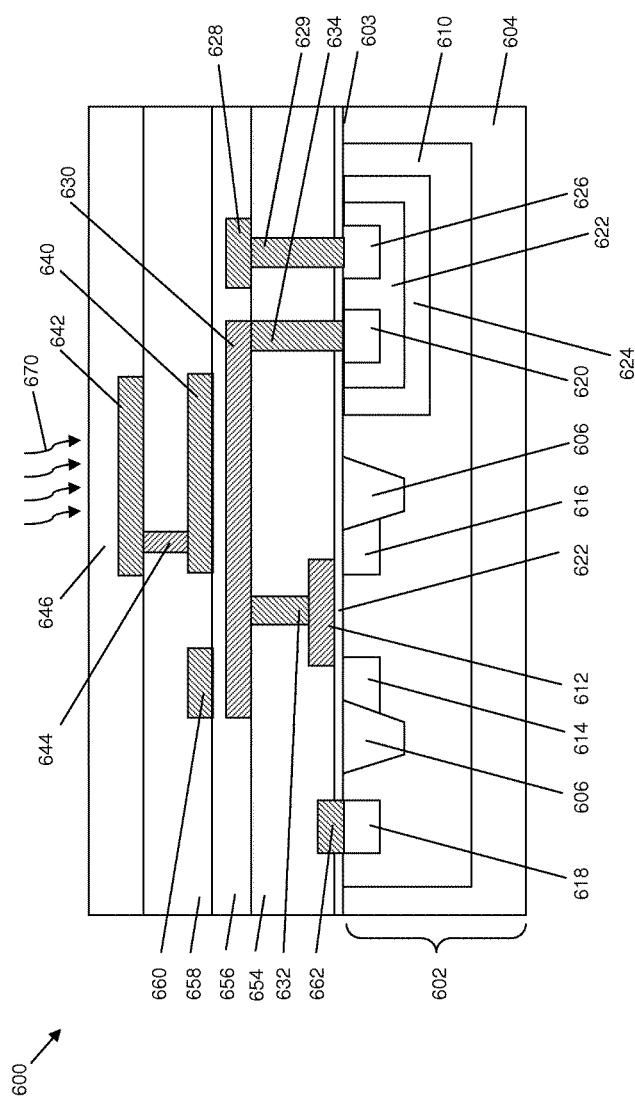
FIG. 6 is a cross-sectional view of an n-channel or p-channel ISFET with a biased series of protection diodes, according to another example embodiment.

In the embodiments of FIGS. 1-3, protection diode circuits that include a single zener or PN junction diode coupled to a floating gate structure are depicted and described. In various alternate embodiments, a protection diode circuit may include more than one diode. For example, various embodiments of protection diode circuits may include multiple diodes coupled in series and/or in parallel in a variety of configurations. In addition, some embodiments of protection diode circuits may include structures that enable biasing of one or more diodes within the protection diode circuit. For example, FIGS. 4-6 illustrate several embodiments of ISFET structures 400, 500, 600, each of which includes a protection diode circuit with a series of protection diodes and a bias structure.

Figure 4:
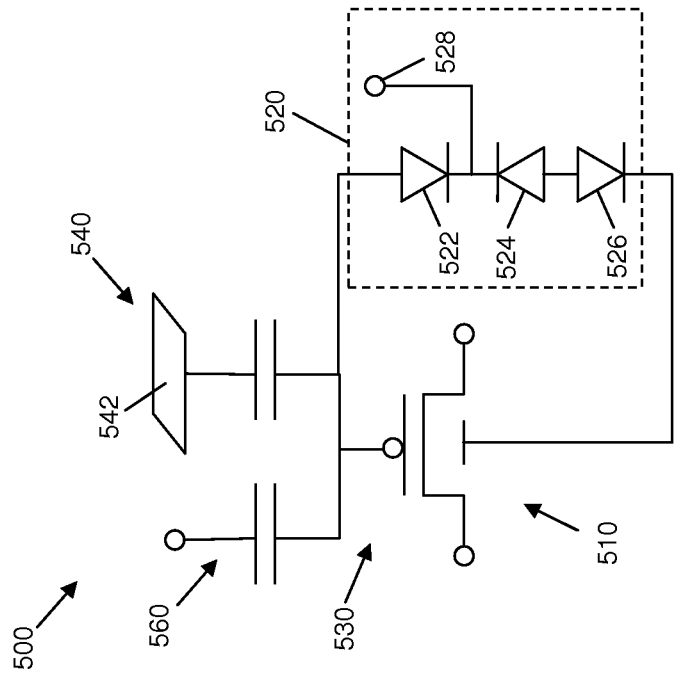
FIG. 4 is a simplified circuit representation of an n-channel ISFET with a biased series of protection diodes, according to another example embodiment.

For example, FIG. 4 is a simplified circuit representation of an n-channel ISFET 400 with a protection diode circuit 420 that includes a biased series of diodes 422, 424, 426 (i.e., a series of diodes that is capable of receiving a bias voltage), according to another example embodiment. More specifically, ISFET 400 includes an n-channel IGFET 410, a floating gate structure 430, a sense plate structure 440, and a protection diode circuit 420. According to an embodiment, ISFET 400 also may include a control gate structure 460, which is capacitively coupled to the floating gate structure 430.

As with IGFET 110 (FIG. 1), IGFET 410 includes a gate, a source region coupled to a source contact, a drain region coupled to a drain contact, and a body region. The gate forms a portion of floating gate structure 430, which also includes one or more conductive structures that are capacitively coupled with sense plate structure 440. Sense plate structure 440 includes a sense plate 442 configured to sense the concentration of a target ion or molecule in a fluid (not illustrated) adjacent to the sense plate 442, and additional conductive structures that facilitate the capacitive coupling between the sense plate structure 440 and the floating gate structure 430. Except as described below, ISFET 400 operates in a manner that is similar to ISFET 100 (FIG. 1).

Protection diode circuit 420 includes first, second, and third series-coupled diodes 422, 424, 426. A cathode of first diode 422 is coupled to the floating gate structure 430 and an anode of first diode 422 is coupled to an anode of second diode 424 and to a bias contact 428. A cathode of second diode 424 is coupled to a cathode of third diode 426, and an anode of third diode 426 is coupled to the body region of IGFET 410, as illustrated in FIG. 4. In an alternate embodiment, third diode 426 may have an anode coupled to another region having the same conductivity type as the body region of IGFET 410. According to an embodiment, each of diodes 422, 424, 426 may be a PN junction diode (e.g., although other types of diodes alternatively may be used). By providing bias contact 428 coupled to the anodes of first and second diodes 422, 424, a bias voltage (negative or positive) may be applied to diodes 422, 424 during operation of ISFET 400. For example, when a negative bias voltage is applied using contact 428, the potential of the floating gate structure 430 may go more negative (e.g., when sensing the concentration of certain target ions or molecules) without forward biasing the first diode 422 than it could without the application of the negative bias voltage. Without the ability to provide a negative bias, the protection diode circuit may undesirably become forward biased when the ISFET attempts to sense the concentration of certain target ions or molecules, and the charge associated with those target ions or molecules may undesirably be discharged through the protection diode circuit. Accordingly, provision of the bias contact 428 enables a wider variety of target ions or molecules to be sensed using ISFET 400. In principle, the control gate structure 460 also or alternatively may be utilized to prevent the first diode 422 from becoming undesirably forward biased during operation, although the use of the control gate structure 460 for this purpose may be difficult, as inappropriate adjustment of the control gate bias (and thus the floating gate voltage) may cause the ISFET 400 to transition outside of an accurate sensing window. In alternate embodiments, a bias voltage also or alternatively could be provided between diodes 424 and 426 (e.g., through a contact (not illustrated) coupled to the cathodes of diodes 424, 426).

FIG. 5 is a simplified circuit representation of a p-channel ISFET 500 with a protection diode circuit 520 that includes a biased series of diodes 522, 524, 526, according to another example embodiment. In contrast with ISFET 400 (FIG. 4), ISFET 500 includes a p-channel IGFET 510, and a protection diode circuit 520 with first, second, and third series-coupled diodes 522, 524, 526 coupled in a reversed configuration from the protection diode circuit 420 of FIG. 4. More specifically, an anode of first diode 522 is coupled to the floating gate structure 530 and a cathode of first diode 522 is coupled to a cathode of second diode 524 and to a bias contact 528. An anode of second diode 524 is coupled to an anode of third diode 526, and a cathode of third diode 526 is coupled to the body region of IGFET 510, as illustrated in FIG. 5. In an alternate embodiment, third diode 526 may have a cathode coupled to another region having the same conductivity type as the body region of IGFET 510. According to an embodiment, each of diodes 522, 524, 526 may be a PN junction diode (although other types of diodes alternatively may be used). By providing bias contact 528 coupled to the cathodes of first and second diodes 522, 524, a bias voltage (negative or positive) may be applied to diodes 522, 524 during operation of ISFET 500. For example, when a positive bias voltage is applied using contact 528, the potential of the floating gate structure 530 may go more positive (e.g., when sensing the concentration of certain target ions or molecules) without forward biasing the first diode 522 than it could without the application of the positive bias voltage. Without the ability to provide a positive bias, the protection diode circuit may undesirably become forward biased when the ISFET attempts to sense the concentration of certain target ions or molecules, and the charge associated with those target ions or molecules may undesirably be discharged through the protection diode circuit. Accordingly, provision of the bias contact 528 enables a wider variety of target ions or molecules to be sensed using ISFET 500. In principle, the control gate structure 560 also or alternatively may be utilized to prevent the first diode 522 from becoming undesirably forward biased during operation although the use of the control gate structure 560 for this purpose may be difficult for reasons explained above. In alternate embodiments, a bias voltage also or alternatively could be provided between diodes 524 and 526 (e.g., through a contact (not illustrated) coupled to the anodes of diodes 524, 526).

Similar to ISFET 400, IGFET 510 also includes a gate that forms a portion of the floating gate structure 530, a source region coupled to a source contact, and a drain region coupled to a drain contact. In addition, ISFET 500 includes a sense plate structure 540 with a sense plate 542, where the sense plate structure 540 is capacitively coupled with the floating gate structure 530. ISFET 500 also may include a control gate structure 560, which is capacitively coupled to the floating gate structure 530.

The circuit representations depicted in FIGS. 4 and 5 may be physically realized using a semiconductor structure, such as the structure depicted in FIG. 6. More specifically, FIG. 6 is a cross-sectional view of an n-channel or p-channel ISFET 600 with a protection diode circuit that includes a series of diodes coupled to a floating gate structure, according to an example embodiment. Similar to ISFET 300, ISFET 600 may be an n-channel device or a p-channel device, depending on the selected conductivities of various regions of ISFET 600.

ISFET 600 is formed in and on a semiconductor substrate 602, which has a top substrate surface 603. The semiconductor substrate 602 includes a base substrate 604 of either the first or second conductivity type, and a well region 610 (or body region) of the first conductivity type. Further, ISFET 600 includes an IGFET formed in and over an active region of the substrate 602. According to an embodiment, the IGFET includes source and drain regions 614, 616 of the second conductivity type formed within well region 610, and spatially separated from each other across the top surface 603 of the substrate 602. The portion of the substrate 602 between the source and drain regions 614, 616 defines a channel region, and the IGFET further includes a gate dielectric 622 and a gate 612 formed over the channel region. The gate 612 may be a polysilicon gate, according to an embodiment. In an alternate embodiment, the gate 612 may be formed from a metal or metal alloy.

The gate 612 forms a portion of a floating gate structure (e.g., floating gate structure 430, 530, FIGS. 4, 5) that is formed in, on, and through one or more dielectric layers 654 overlying the top surface 603 of the substrate 602. The floating gate structure also includes at least one conductor 630 formed in at least one metal layer, and at least one conductive via 632 electrically coupling the conductor(s) 630 to the gate 612.

A sense plate structure (e.g., sense plate structure 440, 540, FIGS. 4, 5) is formed in, on, and through one or more dielectric layers 658 overlying the floating gate structure. According to an embodiment, the sense plate structure includes a metal sense plate 642 that is configured to sense the concentration of a target ion or molecule in a fluid 670 adjacent to a portion of the sense plate 642. According to an embodiment, the sense plate 642 is formed in a top metal layer of the ISFET 600. In order to protect the sense plate 642, a passivation layer 646 may be formed over the sense plate 642. In other embodiments, the passivation layer 646 may be excluded, or other types of layers may be formed over the sense plate 642, as described previously. The sense plate structure also includes at least one conductor 640 formed in at least one metal layer below the layer within which the sense plate 642 is formed, along with at least one conductive via 644 electrically coupling the conductor(s) 640 to the sense plate 642. According to an embodiment, the floating gate structure and the sense plate structure are capacitively coupled through dielectric layer 656, as described previously in conjunction with ISFET 300.

ISFET 600 also includes a protection diode circuit (e.g., protection diode circuit 420, 520, FIGS. 4, 5) electrically coupled to the floating gate structure through one or more conductive vias 634 and possibly other conductive features, in an embodiment. For example, the protection diode circuit may be implemented as a series of PN junction diodes that are electrically coupled between the floating gate structure and the well region 610. According to an embodiment, the series of PN junction diodes are implemented using nested regions of opposite conductivity types. For example, in the embodiment of FIG. 6, the nested regions include a first diode well region 624 of the second conductivity type formed within well region 610, a second diode well region 622 of the first conductivity type formed within the first diode well region 624, and a third diode region 620 of the second conductivity type formed within the second diode well region 622. This nested structure establishes a series of three PN junctions (or three series-coupled PN junction diodes) between the floating gate structure and the well region 610. More specifically, a first PN junction is established between regions 620 and 622, a second PN junction is established between regions 622 and 624, and a third PN junction is established between regions 624 and 610. In an embodiment in which regions 610 and 622 have p-type conductivity and regions 620 and 624 have n-type conductivity (e.g., as in the ISFET embodiment represented by the circuit of FIG. 4), region 620 functions as a cathode of a first diode (e.g., diode 422), region 622 functions as an anode of the first diode and an anode of a second diode (e.g., diode 424), region 624 functions as a cathode of the second diode and a cathode of a third diode (e.g., diode 426), and well region 610 functions as an anode of the third diode. Conversely, in an embodiment in which regions 610 and 622 have n-type conductivity and regions 620 and 624 have p-type conductivity (e.g., as in the ISFET embodiment represented by the circuit of FIG. 5), region 620 functions as an anode of a first diode (e.g., diode 522), region 622 functions as a cathode of the first diode and a cathode of a second diode (e.g., diode 524), region 624 functions as an anode of the second diode and an anode of a third diode (e.g., diode 526), and well region 610 functions as a cathode of the third diode.

According to an embodiment, the protection diode circuit also includes a bias contact (e.g., bias contact 428, 528, FIGS. 4, 5), which enables diode region 622 to receive a bias voltage. For example, the protection diode circuit may include a contact region 626 of the first conductivity type, but more heavily doped than the second diode well region 622. In addition, ISFET 600 may include conductive structures (e.g., one or more conductive lines formed from metal layer 628 and one or more conductive vias 629), which enable a bias voltage to be provided to contact region 626. For example, as mentioned previously, when ISFET 600 is an n-channel device, a negative bias voltage may be provided to contact region 626 to avoid undesirably forward biasing the protection diode during operation when the ISFET 600 is being used to sense the concentration of certain target ions or molecules. Conversely, when ISFET 600 is a p-channel device, a positive bias voltage may be provided to contact region 626 to avoid undesirably forward biasing the protection diode during operation.

In further embodiments, ISFET 600 may include additional features. For example, ISFET 600 also may include body contact region 618 of the first conductivity type and more heavily doped than the well region 610, in an embodiment. In addition, ISFET 600 may also include various STI structures 606 adjacent to the source and drain regions 614, 616, in an embodiment. In an alternate embodiment, the STI structures 606 may be replaced with a silicide blocking layer.

Further, ISFET 600 also may include a control gate structure 660, which is capacitively coupled to the floating gate structure (e.g., to conductor 630 of the floating gate structure). ISFET 600 also may include additional contacts (e.g., a source contact (not illustrated), drain contact (not illustrated), and body contact 662) and other conductive structures that provide for electrical connection of various portions of ISFET 600 to other circuitry (not illustrated).

Figure 9:
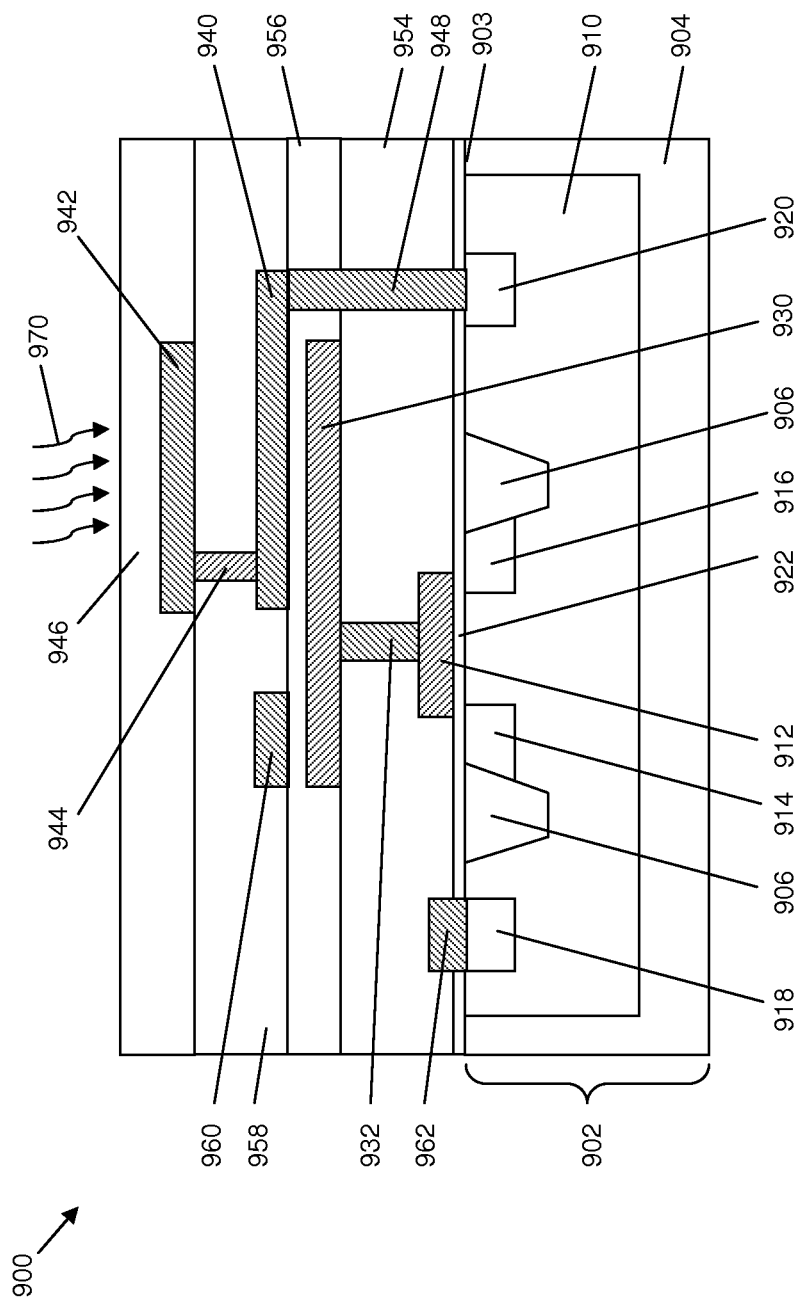
FIG. 9 is a cross-sectional view of an n-channel or p-channel ISFET with a protection diode, according to yet another example embodiment.
Figure 11:
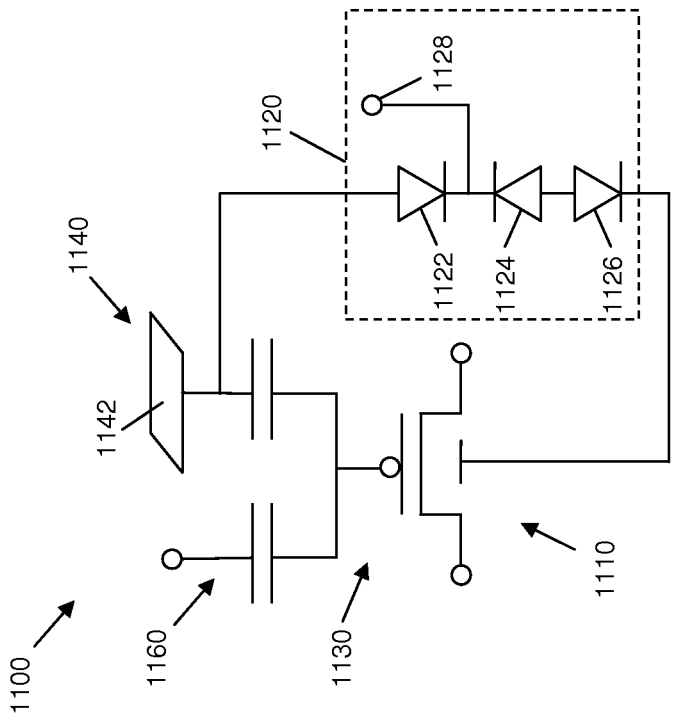
FIG. 11 is a simplified circuit representation of a p-channel ISFET with a biased series of protection diodes, according to yet another example embodiment.
Figure 10:
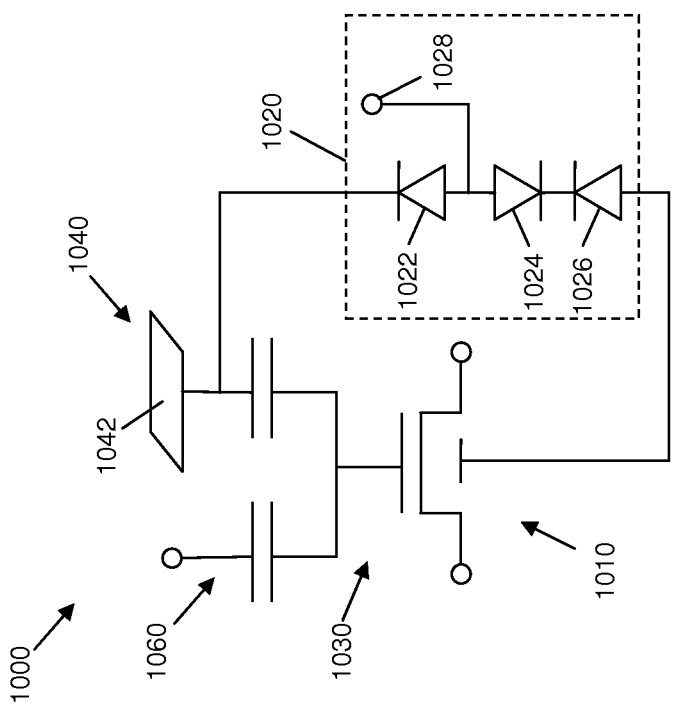
FIG. 10 is a simplified circuit representation of an n-channel ISFET with a biased series of protection diodes, according to yet another example embodiment.
Figure 12:
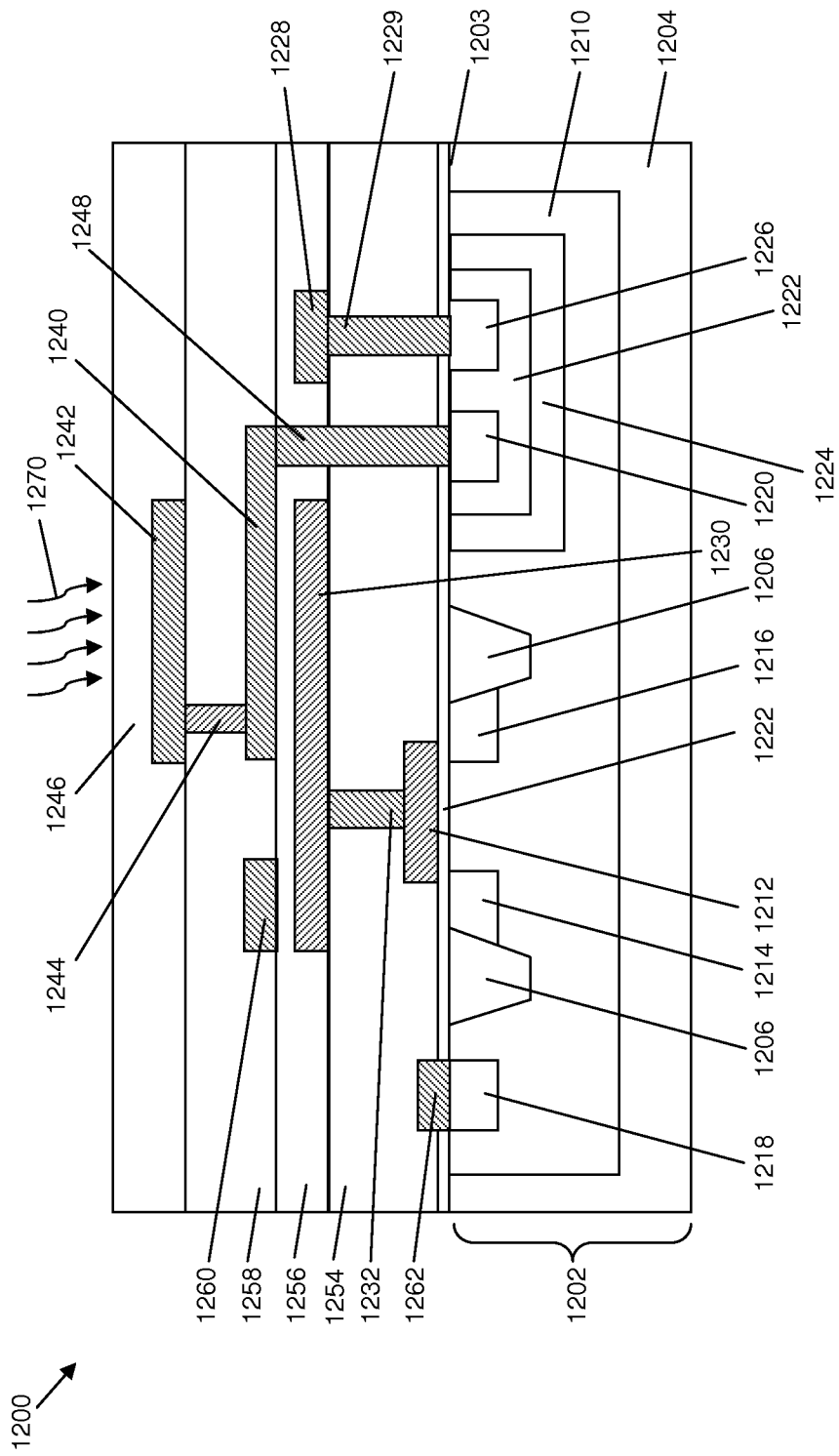
FIG. 12 is a cross-sectional view of an n-channel or p-channel ISFET with a biased series of protection diodes, according to yet another example embodiment.

In the embodiments of FIGS. 1-6, various protection diode circuits that are coupled to the floating gate structure are depicted and described. In various alternate embodiments, a protection diode circuit alternatively may be coupled to the sense plate structure. For example, FIGS. 7-12 illustrate several embodiments of ISFET structures 700, 800, 900, 1000, 1100, 1200, each of which includes a protection diode circuit coupled to a sense plate structure. More specifically, FIGS. 7-9 illustrate embodiments of n-channel and p-channel ISFET structures 700, 800, 900 that include protection diode circuits that include a single PN junction diode (similar to the embodiments of FIGS. 1-3), and FIGS. 10-12 illustrate embodiments of n-channel and p-channel ISFET structures 1000, 1100, 1200 that include protection diode circuits that include multiple, series-connected PN junction diodes (similar to the embodiments of FIGS. 4-6). For purpose of brevity, details of the ISFET structures 700, 800, 900, 1000, 1100, 1200 that are substantively similar to corresponding details of ISFET structures 100, 200, 300, 400, 500, 600 are excluded from the description, below. Such details apply equally to the embodiments of ISFET structures 700, 800, 900, 1000, 1100, 1200 described below.

For example, FIG. 7 is a simplified circuit representation of an n-channel ISFET 700 with a protection diode circuit that includes a protection diode 720, according to another example embodiment. More specifically, ISFET 700 includes an n-channel IGFET 710, a floating gate structure 730, a sense plate structure 740, and a protection diode 720. According to an embodiment, ISFET 700 also may include a control gate structure 760, which is capacitively coupled to the floating gate structure 730.

IGFET 710 also includes a gate, a source region coupled to a source contact, a drain region coupled to a drain contact, and a body region. The gate forms a portion of floating gate structure 730, which also includes one or more conductive structures that are capacitively coupled with sense plate structure 740. Sense plate structure 740 includes a sense plate 742 configured to sense the concentration of a target ion or molecule in a fluid (not illustrated) adjacent to the sense plate 742, and additional conductive structures that facilitate the capacitive coupling between the sense plate structure 740 and the floating gate structure 730.

Protection diode circuit 720 includes diode 720. A cathode of diode 720 is coupled to the sense plate structure 740 and an anode of diode 720 is coupled to the body region of IGFET 710, as illustrated in FIG. 7. In an alternate embodiment, protection diode 720 may have an anode coupled to another region having the same conductivity type as the body region of IGFET 710. According to an embodiment, diode 720 may be a PN junction diode (although other types of diodes alternatively may be used).

FIG. 8 is a simplified circuit representation of a p-channel ISFET 800 with a protection diode circuit that includes a protection diode 820, according to another example embodiment. In contrast with ISFET 700 (FIG. 7), ISFET 800 includes a p-channel IGFET 810, and a protection diode 820 coupled in a reversed configuration from the protection diode 720 of FIG. 7. More specifically, an anode of diode 820 is coupled to the sense plate structure 840 and a cathode of diode 820 is coupled to the body region of IGFET 810, as illustrated in FIG. 8. In an alternate embodiment, protection diode 820 may have a cathode coupled to another region having the same conductivity type as the body region of IGFET 810. According to an embodiment, diode 820 may be a PN junction diode (although other types of diodes alternatively may be used).

Similar to ISFET 700, IGFET 810 also includes a gate that forms a portion of the floating gate structure 830, a source region coupled to a source contact, and a drain region coupled to a drain contact. In addition, ISFET 800 includes the sense plate structure 840 with a sense plate 842, where the sense plate structure 840 is capacitively coupled with the floating gate structure 830. ISFET 800 also may include a control gate structure 860, which is capacitively coupled to the floating gate structure 830.

The circuit representations depicted in FIGS. 7 and 8 may be physically realized using a semiconductor structure, such as the structure depicted in FIG. 9. More specifically, FIG. 9 is a cross-sectional view of an n-channel or p-channel ISFET 900 with a protection diode circuit that includes a PN junction diode coupled to a sense plate structure, according to an example embodiment. ISFET 900 may be an n-channel device or a p-channel device, depending on the selected conductivities of various regions of ISFET 900.

ISFET 900 is formed in and on a semiconductor substrate 902, which has a top substrate surface 903. The semiconductor substrate 902 includes a base substrate 904 of either the first or second conductivity type, and a well region 910 (or body region) of the first conductivity type. Further, ISFET 900 includes an IGFET formed in and over an active region of the substrate 902. According to an embodiment, the IGFET includes source and drain regions 914, 916 of the second conductivity type formed within well region 910, and spatially separated from each other across the top surface 903 of the substrate 902. The portion of the substrate 902 between the source and drain regions 914, 916 defines a channel region, and the IGFET further includes a gate dielectric 922 and a gate 912 formed over the channel region. The gate 912 may be a polysilicon gate, according to an embodiment. In an alternate embodiment, the gate 912 may be formed from a metal or metal alloy.

The gate 912 forms a portion of a floating gate structure (e.g., floating gate structure 730, 830, FIGS. 7, 8) that is formed in, on, and through one or more dielectric layers 954 overlying the top surface 903 of the substrate 902. The floating gate structure also includes at least one conductor 930 formed in at least one metal layer, and at least one conductive via 932 electrically coupling the conductor(s) 930 to the gate 912.

A sense plate structure (e.g., sense plate structure 740, 840, FIGS. 7, 8) is formed in, on, and through one or more dielectric layers 958 overlying the floating gate structure. According to an embodiment, the sense plate structure includes a metal sense plate 942 that is configured to sense the concentration of a target ion or molecule in a fluid 970 adjacent to a portion of the sense plate 942. According to an embodiment, the sense plate 942 is formed in a top metal layer of the ISFET 900. In order to protect the sense plate 942, a passivation layer 946 may be formed over the sense plate 942. In other embodiments, the passivation layer 946 may be excluded, or other types of layers may be formed over the sense plate 942, as described previously. The sense plate structure also includes at least one conductor 940 formed in at least one metal layer below the layer within which the sense plate 942 is formed, along with at least one conductive via 944 electrically coupling the conductor(s) 940 to the sense plate 942. According to an embodiment, the floating gate structure and the sense plate structure are capacitively coupled through dielectric layer 956, as described previously.

ISFET 900 also includes a protection diode circuit (e.g., protection diode circuit 720, 820, FIGS. 7, 8) electrically coupled to the sense plate structure through one or more conductive vias 948 and possibly other conductive features, in an embodiment. For example, the protection diode circuit may be implemented as a PN junction diode (although other types of diodes alternatively may be used) that is electrically coupled between the sense plate structure and the well region 910. According to an embodiment, ISFET 900 includes a diode region 920 of the second conductivity type formed within well region 910, and the PN junction established between diode region 920 and the well region 910 functions as the protection diode. In an embodiment in which the well region 910 has p-type conductivity and the diode region 920 has n-type conductivity (e.g., as in the ISFET embodiment represented by the circuit of FIG. 7), the diode region 920 functions as a cathode of the protection diode. Conversely, in an embodiment in which the well region 910 has n-type conductivity and the diode region 920 has p-type conductivity (e.g., as in the ISFET embodiment represented by the circuit of FIG. 8), the diode region 920 functions as an anode of the protection diode. In an alternate embodiment, a PN junction that functions as a protection diode may include a PN junction between the source and/or drain region 914, 916 and the well region 910. In other words, the source and/or drain regions 914, 916 may function as the cathode or anode of the protection diode, and diode region 920 may be excluded.

In further embodiments, ISFET 900 may include additional features. For example, ISFET 900 also may include body contact region 918 of the first conductivity type and more heavily doped than the well region 910, in an embodiment. In addition, ISFET 900 may also include various STI structures 906 adjacent to the source and drain regions 914, 916, in an embodiment. In an alternate embodiment, the STI structures 906 may be replaced with a silicide blocking layer.

Further, ISFET 900 also may include a control gate structure 960, which is capacitively coupled to the floating gate structure (e.g., to conductor 930 of the floating gate structure). ISFET 900 also may include additional contacts (e.g., a source contact (not illustrated), drain contact (not illustrated), and body contact 962) and other conductive structures that provide for electrical connection of various portions of ISFET 900 to other circuitry (not illustrated).

As mentioned above, further embodiments of ISFETs may include protection diode circuits that include multiple, series-coupled diodes connected to a sense plate structure. For example, FIG. 10 is a simplified circuit representation of an n-channel ISFET 1000 with a protection diode circuit 1020 that includes a biased series of diodes 1022, 1024, 1026, according to another example embodiment. More specifically, ISFET 1000 includes an n-channel IGFET 1010, a floating gate structure 1030, a sense plate structure 1040, and a protection diode circuit 1020. According to an embodiment, ISFET 1000 also may include a control gate structure 1060, which is capacitively coupled to the floating gate structure 1030.

IGFET 1010 includes a gate, a source region coupled to a source contact, a drain region coupled to a drain contact, and a body region. The gate forms a portion of floating gate structure 1030, which also includes one or more conductive structures that are capacitively coupled with sense plate structure 1040. Sense plate structure 1040 includes a sense plate 1042 configured to sense the concentration of a target ion or molecule in a fluid (not illustrated) adjacent to the sense plate 1042, and additional conductive structures that facilitate the capacitive coupling between the sense plate structure 1040 and the floating gate structure 1030.

Protection diode circuit 1020 includes first, second, and third series-coupled diodes 1022, 1024, 1026. A cathode of first diode 1022 is coupled to the sense plate structure 1040 and an anode of first diode 1022 is coupled to an anode of second diode 1024 and to a bias contact 1028. A cathode of second diode 1024 is coupled to a cathode of third diode 1026, and an anode of third diode 1026 is coupled to the body region of IGFET 1010, as illustrated in FIG. 10. In an alternate embodiment, third diode 1026 may have an anode coupled to another region having the same conductivity type as the body region of IGFET 1010. According to an embodiment, each of diodes 1022, 1024, 1026 may be a PN junction diode, although other types of diodes alternatively may be used. As with the previously described embodiments, by providing bias contact 1028 coupled to the anodes of first and second diodes 1022, 1024, a bias voltage may be applied to diodes 1022, 1024 to avoid undesirably forward biasing the protection diode circuit 1020 during operation, as discussed previously. In alternate embodiments, a bias voltage also or alternatively could be provided between diodes 1024 and 1026 (e.g., through a contact (not illustrated) coupled to the cathodes of diodes 1024, 1026).

FIG. 11 is a simplified circuit representation of a p-channel ISFET 1100 with a protection diode circuit 1120 that includes a biased series of diodes 1122, 1124, 1126, according to another example embodiment. In contrast with ISFET 1000 (FIG. 10), ISFET 1100 includes a p-channel IGFET 1110, and a protection diode circuit 1120 with first, second, and third series-coupled diodes 1122, 1124, 1126 coupled in a reversed configuration from the protection diode circuit 1020 of FIG. 10. More specifically, an anode of first diode 1122 is coupled to the sense plate structure 1140 and a cathode of first diode 1122 is coupled to a cathode of second diode 1124 and to a bias contact 1128. An anode of second diode 1124 is coupled to an anode of third diode 1126, and a cathode of third diode 1126 is coupled to the body region of IGFET 1110, as illustrated in FIG. 11. In an alternate embodiment, third diode 1126 may have a cathode coupled to another region having the same conductivity type as the body region of IGFET 1110. According to an embodiment, each of diodes 1122, 1124, 1126 includes a PN junction diode, although other types of diodes alternatively may be used. By providing bias contact 1128 coupled to the cathodes of first and second diodes 1122, 1124, a bias voltage may be applied to diodes 1122, 1124 to avoid undesirably forward biasing the protection diode circuit 1120 during operation, as discussed previously. In alternate embodiments, a bias voltage also or alternatively could be provided between diodes 1124 and 1126 (e.g., through a contact (not illustrated) coupled to the anodes of diodes 1124, 1126).

IGFET 1110 also includes a gate that forms a portion of the floating gate structure 1130, a source region coupled to a source contact, and a drain region coupled to a drain contact. In addition, ISFET 1100 includes a sense plate structure 1140 with a sense plate 1142, where the sense plate structure 1140 is capacitively coupled with the floating gate structure 1130. ISFET 1100 also may include a control gate structure 1160, which is capacitively coupled to the floating gate structure 1130.

The circuit representations depicted in FIGS. 10 and 11 may be physically realized using a semiconductor structure, such as the structure depicted in FIG. 12. More specifically, FIG. 12 is a cross-sectional view of an n-channel or p-channel ISFET 1200 with a protection diode circuit that includes a series of diodes coupled to a sense plate structure, according to an example embodiment. ISFET 1200 may be an n-channel device or a p-channel device, depending on the selected conductivities of various regions of ISFET 1200.

ISFET 1200 is formed in and on a semiconductor substrate 1202, which has a top substrate surface 1203. The semiconductor substrate 1202 includes a base substrate 1204 of either the first or second conductivity type, and a well region 1210 (or body region) of the first conductivity type. Further, ISFET 1200 includes an IGFET formed in and over an active region of the substrate 1202. According to an embodiment, the IGFET includes source and drain regions 1214, 1216 of the second conductivity type formed within well region 1210, and spatially separated from each other across the top surface 1203 of the substrate 1202. The portion of the substrate 1202 between the source and drain regions 1214, 1216 defines a channel region, and the IGFET further includes a gate dielectric 1222 and a gate 1212 formed over the channel region. The gate 1212 may be a polysilicon gate, according to an embodiment. In an alternate embodiment, the gate 1212 may be formed from a metal or metal alloy.

The gate 1212 forms a portion of a floating gate structure (e.g., floating gate structure 1030, 1130, FIGS. 10, 11) that is formed in, on, and through one or more dielectric layers 1254 overlying the top surface 1203 of the substrate 1202. The floating gate structure also includes at least one conductor 1230 formed in at least one metal layer, and at least one conductive via 1232 electrically coupling the conductor(s) 1230 to the gate 1212.

A sense plate structure (e.g., sense plate structure 1040, 1140, FIGS. 10, 11) is formed in, on, and through one or more dielectric layers 1258 overlying the floating gate structure. According to an embodiment, the sense plate structure includes a metal sense plate 1242 that is configured to sense the concentration of a target ion or molecule in a fluid 1270 adjacent to a portion of the sense plate 1242. According to an embodiment, the sense plate 1242 is formed in a top metal layer of the ISFET 1200. In order to protect the sense plate 1242, a passivation layer 1246 may be formed over the sense plate 1242. In other embodiments, the passivation layer 1246 may be excluded, or other types of layers may be formed over the sense plate 1242, as described previously. The sense plate structure also includes at least one conductor 1240 formed in at least one metal layer below the layer within which the sense plate 1242 is formed, along with at least one conductive via 1244 electrically coupling the conductor(s) 1240 to the sense plate 1242. According to an embodiment, the floating gate structure and the sense plate structure are capacitively coupled through dielectric layer 1256, as described previously.

ISFET 1200 also includes a protection diode circuit (e.g., protection diode circuit 1020, 1120, FIGS. 10, 11) electrically coupled to the sense plate structure through one or more conductive vias 1248 and possibly other conductive features, in an embodiment. For example, the protection diode circuit may be implemented as a series of PN junction diodes (although other types of diodes alternatively may be used) that are electrically coupled between the sense plate structure and the well region 1210. According to an embodiment, the series of PN junction diodes are implemented using nested regions of opposite conductivity types. For example, in the embodiment of FIG. 12, the nested regions include a first diode well region 1224 of the second conductivity type formed within well region 1210, a second diode well region 1222 of the first conductivity type formed within the first diode well region 1224, and a third diode region 1220 of the second conductivity type formed within the second diode well region 1222. This nested structure establishes a series of three PN junctions (or three series-coupled PN junction diodes) between the sense plate structure and the well region 1210. More specifically, a first PN junction is established between regions 1220 and 1222, a second PN junction is established between regions 1222 and 1224, and a third PN junction is established between regions 1224 and 1210. In an embodiment in which regions 1210 and 1222 have p-type conductivity and regions 1220 and 1224 have n-type conductivity (e.g., as in the ISFET embodiment represented by the circuit of FIG. 10), region 1220 functions as a cathode of a first diode (e.g., diode 1022), region 1222 functions as an anode of the first diode and an anode of a second diode (e.g., diode 1024), region 1224 functions as a cathode of the second diode and a cathode of a third diode (e.g., diode 1026), and well region 1210 functions as an anode of the third diode. Conversely, in an embodiment in which regions 1210 and 1222 have n-type conductivity and regions 1220 and 1224 have p-type conductivity (e.g., as in the ISFET embodiment represented by the circuit of FIG. 11), region 1220 functions as an anode of a first diode (e.g., diode 1122), region 1222 functions as a cathode of the first diode and a cathode of a second diode (e.g., diode 1124), region 1224 functions as an anode of the second diode and an anode of a third diode (e.g., diode 1126), and well region 1210 functions as a cathode of the third diode.

According to an embodiment, the protection diode circuit also includes a bias contact (e.g., bias contact 1028, 1128, FIGS. 10, 11), which enables diode region 1222 to receive a bias voltage. For example, the protection diode circuit may include a contact region 1226 of the first conductivity type, but more heavily doped than the second diode well region 1222. In addition, ISFET 1200 may include conductive structures (e.g., one or more conductive lines formed from metal layer 1228 and one or more conductive vias 1229), which enable a bias voltage to be provided to contact region 1226. For example, as mentioned previously, when ISFET 1200 is an n-channel device, a negative bias voltage may be provided to contact region 1226 to avoid undesirably forward biasing the protection diode circuit during operation, as discussed previously. Conversely, when ISFET 1200 is a p-channel device, a positive bias voltage may be provided to contact region 1226 to avoid undesirably forward biasing the protection diode circuit during operation, as discussed previously.

In further embodiments, ISFET 1200 may include additional features. For example, ISFET 1200 also may include body contact region 1218 of the first conductivity type and more heavily doped than the well region 1210, in an embodiment. In addition, ISFET 1200 may also include various STI structures 1206 adjacent to the source and drain regions 1214, 1216, in an embodiment. In an alternate embodiment, the STI structures 1206 may be replaced with a silicide blocking layer.

Further, ISFET 1200 also may include a control gate structure 1260, which is capacitively coupled to the floating gate structure (e.g., to conductor 1230 of the floating gate structure). ISFET 1200 also may include additional contacts (e.g., a source contact (not illustrated), drain contact (not illustrated), and body contact 1262) and other conductive structures that provide for electrical connection of various portions of ISFET 1200 to other circuitry (not illustrated).

In the previously described embodiments, a protection diode circuit is coupled to either a floating gate structure or to a sense plate structure. To help in protecting the gate dielectric from damage, the above-described protection diode circuits coupled to the floating gate structure may be particularly useful for discharging charges from the floating gate structure, and the above-described protection diode circuits coupled to the sense plate structure may be particularly useful for discharging charges from the sense plate structure. In still other embodiments, protection diode circuits may be coupled to both the floating gate structure and to the sense plate structure. In such embodiments, any combination of types of protection diode circuits may be used. FIGS. 13-16 include various circuit representations of embodiments of ISFETs 1300, 1400, 1500, 1600 that include the same type of protection diode circuit coupled to both the floating gate structure and to the sense plate structure. Those of skill in the art would understand, based on the description herein, that an embodiment of an ISFET may include differently configured protection diode circuits coupled to each of the floating gate structure and the sense plate structure.

Figures 13, 14:
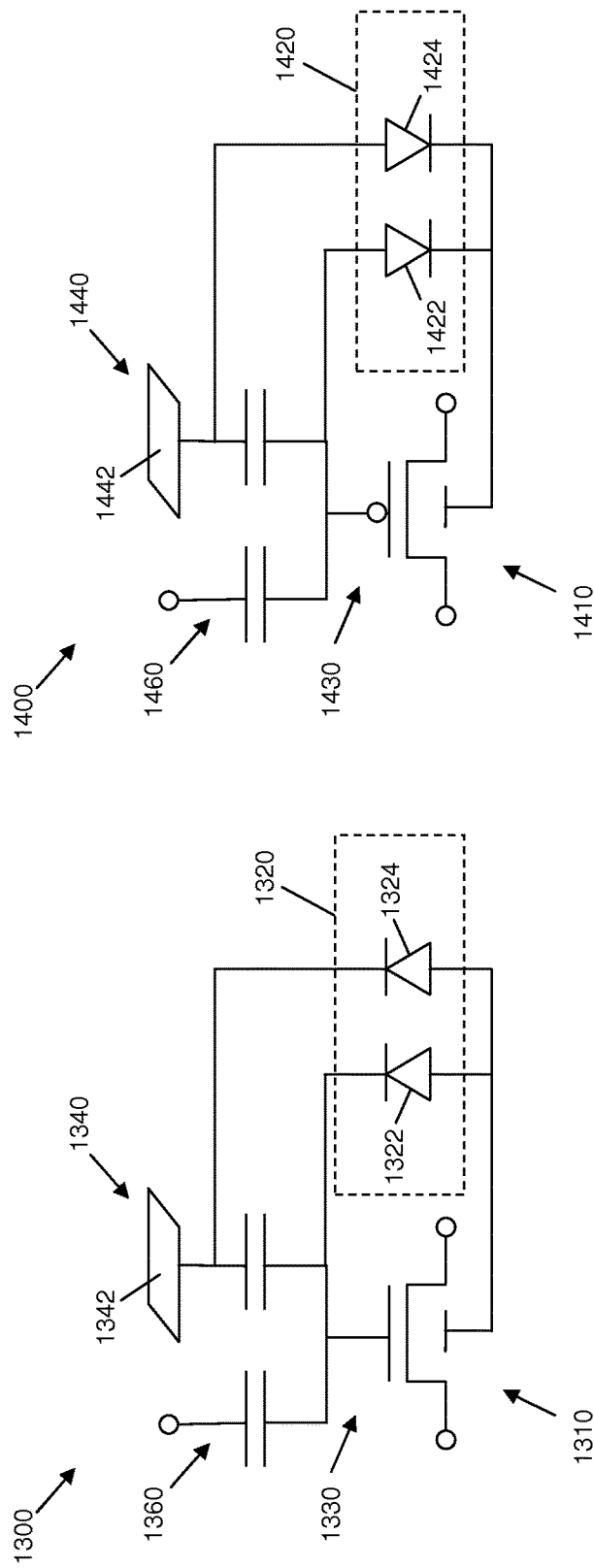
FIG. 13 is a simplified circuit representation of an n-channel ISFET with first and second protection diodes, according to yet another example embodiment.
FIG. 14 is a simplified circuit representation of a p-channel ISFET with first and second protection diodes, according to yet another example embodiment.

FIG. 13 is a simplified circuit representation of an n-channel ISFET 1300 with a protection diode circuit 1320 that includes a first protection diode 1322 coupled to a floating gate structure 1330 and a second protection diode 1324 coupled to a sense plate structure 1340, according to another example embodiment. More specifically, ISFET 1300 includes an n-channel IGFET 1310, a floating gate structure 1330, a sense plate structure 1340, and a protection diode circuit 1320. According to an embodiment, ISFET 1300 also may include a control gate structure 1360, which is capacitively coupled to the floating gate structure 1330.

IGFET 1310 includes a gate, a source region coupled to a source contact, a drain region coupled to a drain contact, and a body region. The gate forms a portion of floating gate structure 1330, which also includes one or more conductive structures that are capacitively coupled with sense plate structure 1340. Sense plate structure 1340 includes a sense plate 1342 configured to sense the concentration of a target ion or molecule in a fluid (not illustrated) adjacent to the sense plate 1342, and additional conductive structures that facilitate the capacitive coupling between the sense plate structure 1340 and the floating gate structure 1330.

Protection diode circuit 1320 includes a first diode 1322 and a second diode 1324. A cathode of the first diode 1322 is coupled to the floating gate structure 1330 and an anode of diode 1322 is coupled to the body region of IGFET 1310 (or to another region having the same conductivity type as the body region of IGFET 1310). Similarly, a cathode of the second diode 1324 is coupled to the sense plate structure 1340 and an anode of diode 1324 is coupled to the body region of IGFET 1310 (or to another region having the same conductivity type as the body region of IGFET 1310). According to an embodiment, diodes 1322, 1324 each include a PN junction diode (although other types of diodes alternatively may be used).

FIG. 14 is a simplified circuit representation of a p-channel ISFET 1400 with a protection diode circuit 1420 that includes a first protection diode 1422 coupled to a floating gate structure 1430 and a second protection diode 1424 coupled to a sense plate structure 1440, according to another example embodiment. In contrast with ISFET 1300 (FIG. 13), ISFET 1400 includes a p-channel IGFET 1410, and protection diodes 1422, 1424 coupled in reversed configurations from the protection diodes 1322, 1324 of FIG. 13. More specifically, an anode of diode 1422 is coupled to the floating gate structure 1430 and a cathode of diode 1422 is coupled to the body region of IGFET 1410 (or to another region having the same conductivity type as the body region of IGFET 1410). In addition, an anode of diode 1424 is coupled to the sense plate structure 1440 and a cathode of diode 1424 is coupled to the body region of IGFET 1410 (or to another region having the same conductivity type as the body region of IGFET 1410). According to an embodiment, diodes 1422, 1424 each include a PN junction diode (although other types of diodes alternatively may be used).

Similar to ISFET 1300, IGFET 1410 also includes a gate that forms a portion of the floating gate structure 1430, a source region coupled to a source contact, and a drain region coupled to a drain contact. In addition, the sense plate structure 1440 includes a sense plate 1442, and the sense plate structure 1440 is capacitively coupled with the floating gate structure 1430. ISFET 1400 also may include a control gate structure 1460, which is capacitively coupled to the floating gate structure 1430.

FIG. 15 is a simplified circuit representation of an n-channel ISFET 1500 with a protection diode circuit 1520 that includes two biased series of diodes 1522, 1524, 1526 and 1523, 1525, 1527, according to another example embodiment. More specifically, ISFET 1500 includes an n-channel IGFET 1510, a floating gate structure 1530, a sense plate structure 1540, and a protection diode circuit 1520. According to an embodiment, ISFET 1500 also may include a control gate structure 1560, which is capacitively coupled to the floating gate structure 1530.

IGFET 1510 includes a gate, a source region coupled to a source contact, a drain region coupled to a drain contact, and a body region. The gate forms a portion of floating gate structure 1530, which also includes one or more conductive structures that are capacitively coupled with sense plate structure 1540. Sense plate structure 1540 includes a sense plate 1542 configured to sense the concentration of a target ion or molecule in a fluid (not illustrated) adjacent to the sense plate 1542, and additional conductive structures that facilitate the capacitive coupling between the sense plate structure 1540 and the floating gate structure 1530.

Protection diode circuit 1520 includes a first set of series-coupled diodes 1522, 1524, 1526 coupled to the floating gate structure 1530, and a second set of series-coupled diodes 1523, 1525, 1527 coupled to the sense plate structure 1540. In the first set of series-coupled diodes, a cathode of first diode 1522 is coupled to the floating gate structure 1530 and an anode of first diode 1522 is coupled to an anode of second diode 1524 and to a first bias contact 1528. A cathode of second diode 1524 is coupled to a cathode of third diode 1526, and an anode of third diode 1526 is coupled to the body region of IGFET 1510 (or to another region having the same conductivity type as the body region of IGFET 1510). In the second set of series-coupled diodes, a cathode of fourth diode 1523 is coupled to the sense plate structure

1540 and an anode of fourth diode 1523 is coupled to an anode of fifth diode 1525 and to a second bias contact 1529. A cathode of fifth diode 1525 is coupled to a cathode of sixth diode 1527, and an anode of sixth diode 1527 is coupled to the body region of IGFET 1510 (or to another region having the same conductivity type as the body region of IGFET 1510). According to an embodiment, each of diodes 1522, 1523, 1524, 1525, 1526, 1527 may be a PN junction diode (although other types of diodes alternatively may be used). As with the previously described embodiments, by providing bias contacts 1528, 1529 coupled to the anodes of first and second diodes 1522, 1524 and fourth and fifth diodes 1523, 1525, one or more bias voltages may be applied to diodes 1522, 1523, 1524, 1525 to define the polarities and/or magnitudes of charges that may be discharged from the floating gate structure 1530 and the sense plate structure 1540 through the protection diode circuit 1520. For example, when negative bias voltages are applied to the bias contacts 1528, 1529, protection diode circuit 1520 may be capable of discharging both positive and negative charges from the floating gate structure 1530 and the sense plate structure 1540 to the ISFET body. In alternate embodiments, a bias voltage also or alternatively could be provided between diodes 1524 and 1526 (e.g., through a contact (not illustrated) coupled to the cathodes of diodes 1524, 1526), and/or between diodes 1525 and 1527 (e.g., through a contact (not illustrated) coupled to the cathodes of diodes 1525, 1527).

FIG. 16 is a simplified circuit representation of a p-channel ISFET 1600 with a protection diode circuit 1620 that includes two biased series of diodes 1622, 1624, 1626 and 1623, 1625, 1627 according to another example embodiment. In contrast with ISFET 1500 (FIG. 15), ISFET 1600 includes a p-channel IGFET 1610, and a protection diode circuit 1620 with two sets of series-coupled diodes 1622, 1624, 1626 and 1623, 1625, 1627 coupled in reversed configurations from the protection diode circuit 1520 of FIG. 15. More specifically, an anode of first diode 1622 is coupled to the floating gate structure 1630 and a cathode of first diode 1622 is coupled to a cathode of second diode 1624 and to a first bias contact 1628. An anode of second diode 1624 is coupled to an anode of third diode 1626, and a cathode of third diode 1626 is coupled to the body region of IGFET 1610 (or to another region having the same conductivity type as the body region of IGFET 1610). In addition, an anode of fourth diode 1623 is coupled to the sense plate structure 1640 and a cathode of fourth diode 1623 is coupled to a cathode of fifth diode 1625 and to a second bias contact 1629. An anode of fifth diode 1625 is coupled to an anode of sixth diode 1627, and a cathode of sixth diode 1627 is coupled to the body region of IGFET 1610 (or to another region having the same conductivity type as the body region of IGFET 1610). According to an embodiment, each of diodes 1622, 1623, 1624, 1625, 1626, 1627 includes a PN junction diode (although other types of diodes alternatively may be used). By providing bias contacts 1628, 1629 coupled to the cathodes of first and second diodes 1622, 1624, and fourth and fifth diodes 1623, 1625, one or more bias voltages may be applied to diodes 1622, 1623, 1624, 1625 to define the polarities and/or magnitudes of charges that may be discharged from the floating gate structure 1630 and the sense plate structure 1640 through the protection diode circuit 1620. For example, when positive bias voltages are applied to the bias contacts 1628, 1629, protection diode circuit 1620 may be capable of discharging both positive and negative charges from the floating gate structure 1630 and the sense plate structure 1640 to the ISFET body. In alternate embodiments, a bias voltage also or alternatively could be provided between diodes 1624 and 1626 (e.g., through a contact (not illustrated) coupled to the anodes of diodes 1624, 1626), and/or between diodes 1525 and 1527 (e.g., through a contact (not illustrated) coupled to the anodes of diodes 1625, 1627).

IGFET 1610 also includes a gate that forms a portion of the floating gate structure 1630, a source region coupled to a source contact, and a drain region coupled to a drain contact. In addition, ISFET 1600 includes the sense plate structure 1640 with a sense plate 1642, where the sense plate structure 1640 is capacitively coupled with the floating gate structure 1630. ISFET 1600 also may include a control gate structure 1660, which is capacitively coupled to the floating gate structure 1630.

The circuit representations depicted in FIGS. 13-16 may be physically realized using semiconductor structures that are combinations of the various structures depicted in FIGS. 3, 6, 9, and 12. For purposes of brevity, figures depicting such semiconductor structures are not included herein. Those of skill in the art would understand, based on the description herein, how to modify the structures of FIGS. 3, 6, 9, and 12 to physically realize the circuit representations depicted in FIGS. 13-16, as well as other circuit representations that include combinations of different protection diode circuits coupled to the floating gate structures and the sense plate structures.

Figure 17:
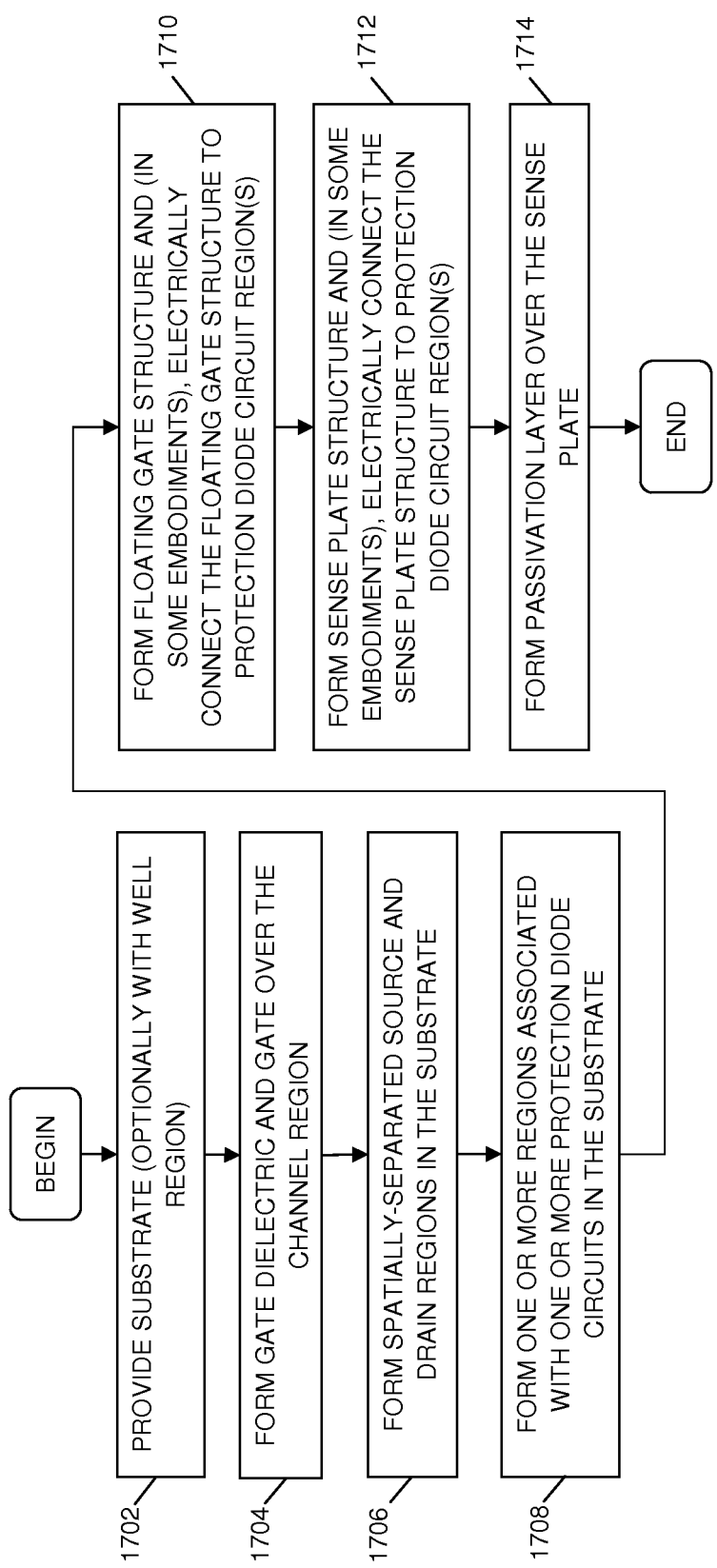
FIG. 17 is a flowchart of a method for fabricating an ISFET with one or more protection diode circuits, according to an example embodiment.

FIG. 17 is a flowchart of a method for fabricating an ISFET with one or more protection diode circuits, according to an example embodiment. Although the various ISFET embodiments described herein are new, the ISFET embodiments described herein may be produced using known semiconductor processing techniques, in particular, well-known CMOS techniques. Further, a variety of well known and common semiconductor materials may be used, (e.g., traditional metals, polysilicon, silicon dioxide, silicon nitride, silicon, and the like). For purpose of brevity, the details regarding such techniques and materials are not discussed in detail herein.

According to an embodiment, fabricating an ISFET may begin, in block 1702, by providing a substrate of a first conductivity type, or by providing a substrate of any conductivity type within which a well of a first conductivity type is formed. The method may continue, in block 1704, by forming a gate dielectric and a gate (e.g., a polysilicon or metal gate) on the surface of the substrate over an area that will be the channel region of the IGFET.

In block 1706, source and drain regions of a second conductivity type are formed within the substrate, where the source and drain regions are spatially separated across a surface of the substrate by the channel region. In addition, the method includes forming one or more regions associated with one or more protection diode circuits within the substrate in block 1708. As discussed previously, in various embodiments, the regions associated with the protection diode circuit(s) may include as few as one region associated with a single protection diode (e.g., as in the embodiments of FIGS. 1-3 and 7-9), or multiple regions associated with multiple protection diodes that are coupled together in series (e.g., as in the embodiments of FIGS. 4-6 and 10-12) and/or that are coupled to different conductive structures (e.g., as in the embodiments of FIGS. 13-16). Some of the regions associated with the protection diode circuit(s) may be formed in parallel with forming the source and drain regions. Alternatively, some of the regions associated with the protection diode circuit(s) may be formed before or after formation of the source and drain regions.

In block 1710, remaining portions of a floating gate structure are formed in, through, and on one or more dielectric layers over the top surface of the substrate. As discussed previously, the floating gate structure includes the gate formed over the gate dielectric, along with additional conductive structures coupled to the gate. In embodiments in which the floating gate structure is coupled to a protection diode circuit (e.g., the embodiments of FIGS. 1-6 and 13-16), the floating gate structure is electrically connected to previously-formed regions within the semiconductor substrate that are associated with the protection diode circuit. In various embodiments, electrically coupling the floating gate structure to the protection circuit may be performed simultaneously with forming the floating gate structure or after forming the floating gate structure.

In block 1712, a sense plate structure is formed in, through, and on one or more dielectric layers over the layers within which the floating gate structure is formed. As discussed previously, the sense plate structure may be formed so that it is capacitively coupled with the floating gate structure. In embodiments in which the sense plate structure is coupled to a protection diode circuit (e.g., the embodiments of FIGS. 7-16), the sense plate structure is electrically connected to previously-formed regions within the semiconductor substrate that are associated with the protection diode circuit. In various embodiments, electrically coupling the sense plate structure to the protection circuit may be performed simultaneously with forming the sense plate structure or after forming the sense plate structure. Once the sense plate structure has been formed, a passivation layer may be formed over the sense plate, in block 1714, in order to protect the sense plate. In other embodiments, the passivation layer may be excluded, or other types of layers may be formed over the sense plate, as described previously.

Although not specifically discussed, the process of forming the ISFET may include a number of other processes as well as those briefly discussed above. Such processes may include forming various contacts and conductive interconnects, forming other circuitry on the same substrate as the ISFET, forming other ISFETs, and so on. In addition, it should be understood that various processes may be performed in different orders than the order depicted in FIG. 17, and/or some processes may be performed in multiple steps and/or in parallel with other processes. Such alternate methods are intended to be included within the scope of the inventive subject matter.

Various embodiments of ISFETs with protection diode circuits and methods of their formation have been described herein. An embodiment of an ISFET structure includes a substrate, source and drain regions formed within the substrate and spatially separated by a channel region, a gate dielectric and a gate formed over the channel region, multiple conductive structures overlying the surface of the substrate, and a protection diode circuit coupled between one of the multiple conductive structures and the substrate. The multiple conductive structures include a floating gate structure and a sense plate structure. The floating gate structure is formed over the gate dielectric and includes the gate. The sense plate structure is electrically coupled to the floating gate structure and is configured to sense a concentration of a target ion or molecule in a fluid adjacent to a portion of the sense plate structure.

Another embodiment of an ISFET structure includes a substrate, source and drain regions formed within the substrate and spatially separated across the surface of the substrate by a channel region, a gate dielectric formed on the surface of the substrate over the channel region, a gate formed on the gate dielectric, a floating gate structure formed over the gate dielectric and including the gate, a sense plate structure electrically coupled to the floating gate structure and configured to sense a concentration of a target ion or molecule in a fluid adjacent to a portion of the sense plate structure, and a protection diode circuit coupled between the floating gate structure and the substrate. The protection diode circuit comprises at least one PN junction between a first set of adjacent regions of opposite conductivity type formed within the substrate.

An embodiment of a method of fabricating an ISFET structure includes forming a gate dielectric and a gate on a surface of a substrate over a channel region, forming a source region and a drain region within the substrate, which are spatially separated across the surface of the substrate by the channel region, forming a protection diode circuit, forming multiple conductive structures overlying the surface of the substrate, and electrically connecting the first protection diode circuit to one of the multiple conductive structures. The multiple conductive structures include a floating gate structure coupled to and including the gate, and a sense plate structure electrically coupled to the floating gate structure and configured to sense a concentration of a target ion or molecule in a fluid adjacent to a portion of the sense plate structure.

While at least one exemplary embodiment has been presented in the foregoing detailed description, it should be appreciated that a vast number of variations exist, especially with respect to choices of device types, materials and doping. It should be appreciated that the exemplary embodiment or exemplary embodiments are only examples, and are not intended to limit the scope, applicability, or configuration of the embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope of the inventive subject matter as set forth in the appended claims and the legal equivalents thereof.

What is claimed is:

1. An Ion Sensitive Field Effect Transistor (ISFET) structure comprising:
   a substrate having a surface, wherein the substrate includes a first region of a first conductivity type that extends to the surface of the substrate;
   a source region and a drain region formed within the substrate and spatially separated across the surface of the substrate by a channel region, wherein the source region and the drain region are regions of a second conductivity type formed within the first region;
   a gate dielectric formed on the surface of the substrate over the channel region;
   a gate formed on the gate dielectric;
   multiple conductive structures overlying the surface of the substrate, wherein the multiple conductive structures include
      a floating gate structure formed over the gate dielectric and including the gate, and
      a sense plate structure electrically coupled to the floating gate structure and configured to sense a concentration of a target ion or molecule in a fluid adjacent to a portion of the sense plate structure; and
   a first protection diode circuit coupled between one of the multiple conductive structures and the substrate, wherein the first protection diode circuit comprises a first well region of the second conductivity type formed within the first region,
a second well region of the first conductivity type formed within the first well region,
a second region of the second conductivity type formed within the second well region,
at least one PN junction between the first and second well regions and the second region, including a first PN junction formed between the first region and the first well region, a second PN junction formed between the first well region and the second well region, and a third PN junction formed between the second well region and the second region, wherein the at least one PN junction correspond to first and second diodes of multiple series-coupled diodes, wherein a first type of terminal of the first diode of the multiple series-coupled diodes is coupled to the one of the multiple conductive structures, and a second type of terminal of the first diode is connected to the second type of terminal of the second diode of the multiple series-coupled diodes, and
a bias contact coupled to a terminal of the first or second diode, whereas the bias contact is configured to provide a bias voltage to the first protection diode circuit that alters a point at which a PN junction of the first protection diode circuit becomes forward biased to avoid discharging charges associated with the target ion or molecule through the first protection diode circuit.

2. The ISFET structure of claim 1, wherein:
the first protection diode circuit is coupled to the floating gate structure, and
the ISFET structure further comprises:
a second protection diode circuit coupled to the sense plate structure, wherein the second protection diode circuit comprises at least one second PN junction between a second set of adjacent regions of opposite conductivity type formed within the substrate.

3. The ISFET structure of claim 1, wherein the first protection diode circuit further comprises:
a third region of the first conductivity type formed within the second well region, and wherein the ISFET structure further comprises:
a contact coupled to the third region and configured to receive a voltage to bias the second well region.

4. The ISFET structure of claim 1, wherein the sense plate structure comprises:
a conductive sense plate formed from a first metal layer proximate a surface of the ISFET structure;
a first metal conductor formed in a second metal layer underlying the first metal layer; and
at least one conductive via electrically coupling the first metal conductor and the sense plate.

5. The ISFET structure of claim 4, wherein the floating gate structure comprises:
the gate formed on the gate dielectric;
a second metal conductor formed in a third metal layer underlying the second metal layer; and
at least one conductive via electrically coupling the second metal conductor and the gate.

6. The ISFET structure of claim 5, further comprising:
an oxide layer formed between the first and second metal conductors, wherein the first and second metal conductors and the oxide layer function to capacitively couple the sense plate structure and the floating gate structure.

7. The ISFET structure of claim 5, wherein the gate is a polysilicon gate.

8. The ISFET structure of claim 1, further comprising:
at least one control gate structure electrically coupled to the floating gate structure, the control gate structure configured to accept a voltage bias and to cause the movement of charge between the floating gate structure and the control gate structure in response to the voltage bias.

9. The ISFET structure of claim 1, wherein the first type of terminal is an anode and the second type of terminal is a cathode.

10. The ISFET structure of claim 1, wherein the first type of terminal is a cathode and the second type of terminal is an anode.

11. An Ion Sensitive Field Effect Transistor (ISFET) structure comprising:
a substrate having a surface, wherein the substrate includes a first region of a first conductivity type that extends to the surface of the substrate;
a source region and a drain region formed within the substrate and spatially separated across the surface of the substrate by a channel region, wherein the source region and the drain region are regions of a second conductivity type formed within the first region;
a gate dielectric formed on the surface of the substrate over the channel region;
a gate formed on the gate dielectric;
a floating gate structure formed over the gate dielectric and including the gate;
a sense plate structure electrically coupled to the floating gate structure and configured to sense a concentration of a target ion or molecule in a fluid adjacent to a portion of the sense plate structure; and
a first protection diode circuit coupled between the floating gate structure and the substrate, wherein the first protection diode circuit comprises at least one PN junction between a first set of adjacent regions of opposite conductivity type formed within the substrate, and wherein the first protection diode circuit comprises
a first well region of the second conductivity type formed within the first region,
a second well region of the first conductivity type formed within the first well region,
a second region of the second conductivity type formed within the second well region, wherein the at least one PN junction includes a first PN junction formed between the first region and the first well region, a second PN junction formed between the first well region and the second well region, and a third PN junction formed between the second well region and the second region, wherein the at least one PN junction correspond to first and second diodes of multiple series-coupled diodes, wherein a first type of terminal of the first diode of the multiple series-coupled diodes is coupled to the floating gate structure, and a second type of terminal of the first diode is connected to a second type of terminal of the second diode of the multiple series-coupled diodes, and
a bias contact coupled to a terminal of the first or second diode, whereas the bias contact is configured to provide a bias voltage to the first protection diode circuit that alters a point at which a PN junction of the at least one PN junction becomes forward biased to avoid discharging charges associated with the target ion or molecule through the first protection diode circuit.

12. The ISFET structure of claim 11, further comprising:
a second protection diode circuit coupled to the sense plate structure, wherein the second protection diode circuit comprises at least one second PN junction between a second set of adjacent regions of opposite conductivity type formed within the substrate.

13. The ISFET structure of claim 11, wherein the first protection diode circuit further comprises:
a third region of the first conductivity type formed within the second well region, and wherein the ISFET structure further comprises:
a contact coupled to the third region and configured to receive a voltage to bias the second well region.

14. A method of fabricating an Ion Sensitive Field Effect Transistor (ISFET) structure, the method comprising the steps of:
forming a gate dielectric and a gate on a surface of a substrate over a channel region, wherein the substrate includes a first region of a first conductivity type that extends to the surface of the substrate;
forming a source region and a drain region of a second conductivity type within the first region, wherein the source region and the drain region are spatially separated across the surface of the substrate by the channel region;
forming a first protection diode circuit by
forming a first well region of the second conductivity type within the first region,
forming a second well region of the first conductivity type within the first well region, and
forming a second region of the second conductivity type within the second well region,
wherein the first and second well regions and the second region form at least one PN junction that includes a first PN junction formed between the first region and the first well region, a second PN junction formed between the first well region and the second well region, and a third PN junction formed between the second well region and the second region, wherein the at least one PN junction correspond to first and second diodes of multiple protection diodes,
wherein each of the multiple protection diodes has a first type of terminal and a second type of terminal, and the second type of terminal of the first diode of the multiple protection diodes is connected to the second type of terminal of the second diode of the multiple protection diodes;
forming multiple conductive structures overlying the surface of the substrate, wherein the multiple conductive structures include
a floating gate structure coupled to and including the gate, and
a sense plate structure electrically coupled to the floating gate structure and configured to sense a concentration of a target ion or molecule in a fluid adjacent to a portion of the sense plate structure;
electrically coupling the first type of terminal of the first diode of the multiple protection diodes to one of the multiple conductive structures; and
electrically coupling a contact to the second type of terminal of the first diode, wherein the contact is configured to receive a voltage to bias the first protection diode circuit in order to alter a point at which a PN junction of the first protection diode circuit becomes forward biased to avoid discharging charges associated with the target ion or molecule through the first protection diode circuit.

15. The method of fabricating an ISFET structure of claim 14, further comprising:
forming a second protection diode circuit, wherein the second protection diode circuit includes at least one second PN junction between a second set of adjacent regions of opposite conductivity type formed within the substrate; and
electrically connecting the second protection diode circuit to the sense plate structure.

16. The method of fabricating an ISFET structure of claim 14, wherein:
forming the first protection diode circuit further comprises forming a third region of the first conductivity type within the second well region; and
electrically coupling the contact to the first protection diode circuit comprises:
electrically coupling the contact to the third region.

* * * * *